(12) United States Patent
Nakayama

(10) Patent No.: US 9,293,892 B2
(45) Date of Patent: Mar. 22, 2016

(54) SHORT OPTICAL PULSE GENERATOR, TERAHERTZ WAVE GENERATION DEVICE, CAMERA, IMAGING APPARATUS, AND MEASUREMENT APPARATUS

(71) Applicant: SEIKO EPSON CORPORATION, Tokyo (JP)

(72) Inventor: Hitoshi Nakayama, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 258 days.

(21) Appl. No.: 14/015,216

(22) Filed: Aug. 30, 2013

(65) Prior Publication Data

US 2014/0061470 A1    Mar. 6, 2014

(30) Foreign Application Priority Data

Sep. 5, 2012  (JP) ................. 2012-194838

(51) Int. Cl.
| | |
|---|---|
| G01J 5/20 | (2006.01) |
| H01L 27/14 | (2006.01) |
| H01L 31/00 | (2006.01) |
| H01S 5/343 | (2006.01) |
| H04N 5/30 | (2006.01) |
| G01N 21/84 | (2006.01) |
| H01S 5/00 | (2006.01) |

(Continued)

(52) U.S. Cl.
CPC ............... *H01S 5/343* (2013.01); *B82Y 20/00* (2013.01); *G01N 21/84* (2013.01); *H01S 5/0057* (2013.01); *H01S 5/026* (2013.01); *H01S 5/0604* (2013.01); *H01S 5/1032* (2013.01); *H04N 5/30* (2013.01); *G01N 21/3581* (2013.01); *H01S 5/0602* (2013.01); *H01S 5/065* (2013.01); *H01S 5/12* (2013.01); *H01S 5/34353* (2013.01)

(58) Field of Classification Search
CPC ...................................................... G01N 21/84
USPC ........................................... 250/338.1, 338.4
See application file for complete search history.

(56) References Cited

U.S. PATENT DOCUMENTS 6,356,693 B1 *  3/2002  Shimizu et al. ............... 385/131
6,519,270 B1 *  2/2003  Kim et al. ....................... 372/28

(Continued)

FOREIGN PATENT DOCUMENTS

| EP | 2 500 713 A2 | 9/2012 |
|---|---|---|
| JP | 3014039 B | 8/1998 |

(Continued)

OTHER PUBLICATIONS

Extended European Search Report dated Apr. 29, 2015 as received in Application No. 13182773.5.

(Continued)

*Primary Examiner* — David Porta
*Assistant Examiner* — Meenakshi Sahu
(74) *Attorney, Agent, or Firm* — Maschoff Brennan

(57) ABSTRACT

A short optical pulse generator which includes an optical pulse generation portion that has a quantum well structure and generates an optical pulse, a frequency chirp portion that has a quantum well structure and chirps a frequency of the optical pulse, and a group velocity dispersion portion that includes a plurality of optical waveguides disposed in a mode coupling distance and which causes a group velocity difference corresponding to a wavelength in the optical pulse of which the frequency is chirped.

20 Claims, 20 Drawing Sheets

(51) Int. Cl.
  *H01S 5/026*   (2006.01)
  *H01S 5/10*    (2006.01)
  *B82Y 20/00*   (2011.01)
  *H01S 5/065*   (2006.01)
  *H01S 5/12*    (2006.01)
  *H01S 5/06*    (2006.01)
  *G01N 21/3581* (2014.01)

(56) References Cited

U.S. PATENT DOCUMENTS 6,954,575 B2    10/2005  Fermann et al.
2012/0236155 A1  9/2012  Nakayama

FOREIGN PATENT DOCUMENTS

| JP | 3328881 B2   | 12/2000 |
| JP | 2006-170822 A | 6/2006  |
| JP | 2009-158983 A | 7/2009  |
| JP | 2010-151562 A | 7/2010  |
| JP | 2012-195545 A | 10/2012 |

OTHER PUBLICATIONS

Flynn et al., "Integrated chirp compensation in a monolithic passively mode-locked semiconductor diode laser", Applied Phystcs Letters, vol. 86, Issue 22, May 25, 2005, pp. 221104-1-221104-2.

Heck, "Ultrafast integrated semiconductor laser technology at 1.55 μm", Technische Universiteit Eindhoven, Jan. 9, 2008, pp. 1-156.

Lee et al., "Applying a mode Selector fo Improve the Pulse-Compression Performance of Asymmetric-Coupled-Waveguide-Based Dispersion Compensators", Opticai Review, vol. 10, Issue 1, Jan. 1, 2003, pp. 38-42.

Lee, "A Semiconductor Coupled-Waveguide Structure as a Dispersion Compensator", Japanese Journal of Applied Physics, vol. 39, Part 1, Issue. 3A, Mar. 1, 2000, pp. 1140-1145.

Lee, "Coupled-weveguide-based semiconductor dispersion compensators", Proceedings of SPIE, vol. 3940, Mar. 28, 2000, pp. 173-183.

Lee, "Pulse compression using coupled-waveguide structures as highly dispersive elements", Applied Physics Letters, vol. 73, Issue 19, Nov. 9, 1998, pp. 2715-2717.

Murata et al., "Optical Pulse Generation by Electrooptic-Modulation Method and Its Application to Integrated Ultrashort Pulse Generators", IEEE Journal on Selected Topics in Quantum Electronics, vol. 6, Issue 6, Nov./Dec. 2000, pp. 1325-1331.

\* cited by examiner

SHORT OPTICAL PULSE GENERATOR, TERAHERTZ WAVE GENERATION DEVICE, CAMERA, IMAGING APPARATUS, AND MEASUREMENT APPARATUS

PRIORITY INFORMATION

The present invention claims priority to Japanese Patent Application No. 2012-194838 filed Sep. 5, 2012, which is incorporated herein by reference in its entirety.

BACKGROUND

1. Technical Field

The present invention relates to a short optical pulse generator, a terahertz wave generation device, a camera, an imaging apparatus, and a measurement apparatus.

2. Related Art

In recent years, a terahertz wave which is an electromagnetic wave with a frequency of 100 GHz or more and 30 THz or less has attracted attention. The terahertz wave may be used for, for example, imaging, a variety of measurements such as spectroscopic measurement, nondestructive inspection, and the like.

A terahertz wave generation device generating the terahertz wave includes, for example, a short optical pulse generator which generates an optical pulse with a pulse width of about subpicoseconds (several hundreds of femtoseconds), and a photoconductive antenna which generates a terahertz wave by being irradiated with the optical pulse generated by the short optical pulse generator. Generally, a femtosecond fiber laser or a Ti-sapphire laser is used as a short optical pulse generator generating an optical pulse with a pulse width of about subpicoseconds.

For example, Japanese Patent Application No. JP-A-2009-158983 discloses a fiber laser capable of generating a linearly chirped high power parabolic pulse by using a fiber doped with a rare-earth element.

However, in the fiber laser disclosed in JP-A-2009-158983, it is necessary to increase fiber length in order to give a predetermined frequency chirp to an optical pulse, and this increase in fiber length results in an increase in the size of the device.

BRIEF SUMMARY OF THE INVENTION

An advantage of some aspects of the invention is to provide a short optical pulse generator, a terahertz wave generation device, a camera, an imaging apparatus, and a measurement apparatus with a smaller size that other known configurations.

An aspect of the invention is directed to a short optical pulse generator including an optical pulse generation portion that has a quantum well structure and generates an optical pulse, a frequency chirp portion that has a quantum well structure and chirps a frequency of the optical pulse, and a group velocity dispersion portion that includes a plurality of optical waveguides disposed in a mode coupling distance and which causes a group velocity difference corresponding to a wavelength in the optical pulse of which the frequency is chirped.

According to the short optical pulse generator, the frequency chirp portion has a quantum well structure. A semiconductor material having a quantum well structure has a larger nonlinear refractive index than, for example, a quartz optical fiber, and thus it is possible to increase a frequency chirp value (frequency variation amount) per unit length. Therefore, it is possible to minimize a frequency chirp portion and to thereby reduce the overall size of the device.

Another aspect of the invention is directed to a terahertz wave generation device including the short optical pulse generator, and a photoconductive antenna that is irradiated with a short optical pulse generated by the short optical pulse generator so as to generate a terahertz wave.

Still another aspect of the invention is directed to a camera including the short optical pulse generator, a photoconductive antenna that is irradiated with a short optical pulse generated by the short optical pulse generator so as to generate a terahertz wave, a terahertz wave detection unit that detects the terahertz wave emitted from the photoconductive antenna and transmitted through an object or reflected by the object, and a storage unit that stores a detection result from the terahertz wave detection unit.

Yet another aspect of the invention is directed to an imaging apparatus including the short optical pulse generator, a photoconductive antenna that is irradiated with a short optical pulse generated by the short optical pulse generator so as to generate a terahertz wave, a terahertz wave detection unit that detects the terahertz wave emitted from the photoconductive antenna and transmitted through an object or reflected by the object, and an image forming unit that generates an image of the object based on a detection result from the terahertz wave detection unit.

Still yet another aspect of the invention is directed to a measurement apparatus including the short optical pulse generator, a photoconductive antenna that is irradiated with a short optical pulse generated by the short optical pulse generator so as to generate a terahertz wave, a terahertz wave detection unit that detects the terahertz wave emitted from the photoconductive antenna and transmitted through an object or reflected by the object, and a measurement unit that measures the object based on a detection result from the terahertz wave detection unit.

In the resulting terahertz wave generation device, camera, imaging apparatus, and measurement apparatus, the resulting apparatus includes the short optical pulse generator and thus can be reduced in size and structure.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments of the invention will be described in detail with reference to the drawings. In addition, the embodiments described below are not intended to improperly limit content of the invention recited in the appended claims. Further, all constituent elements described below are not essential constituent elements of the invention.

1. First Embodiment 1.1 Configuration of Short Optical Pulse Generator

Figure 1:
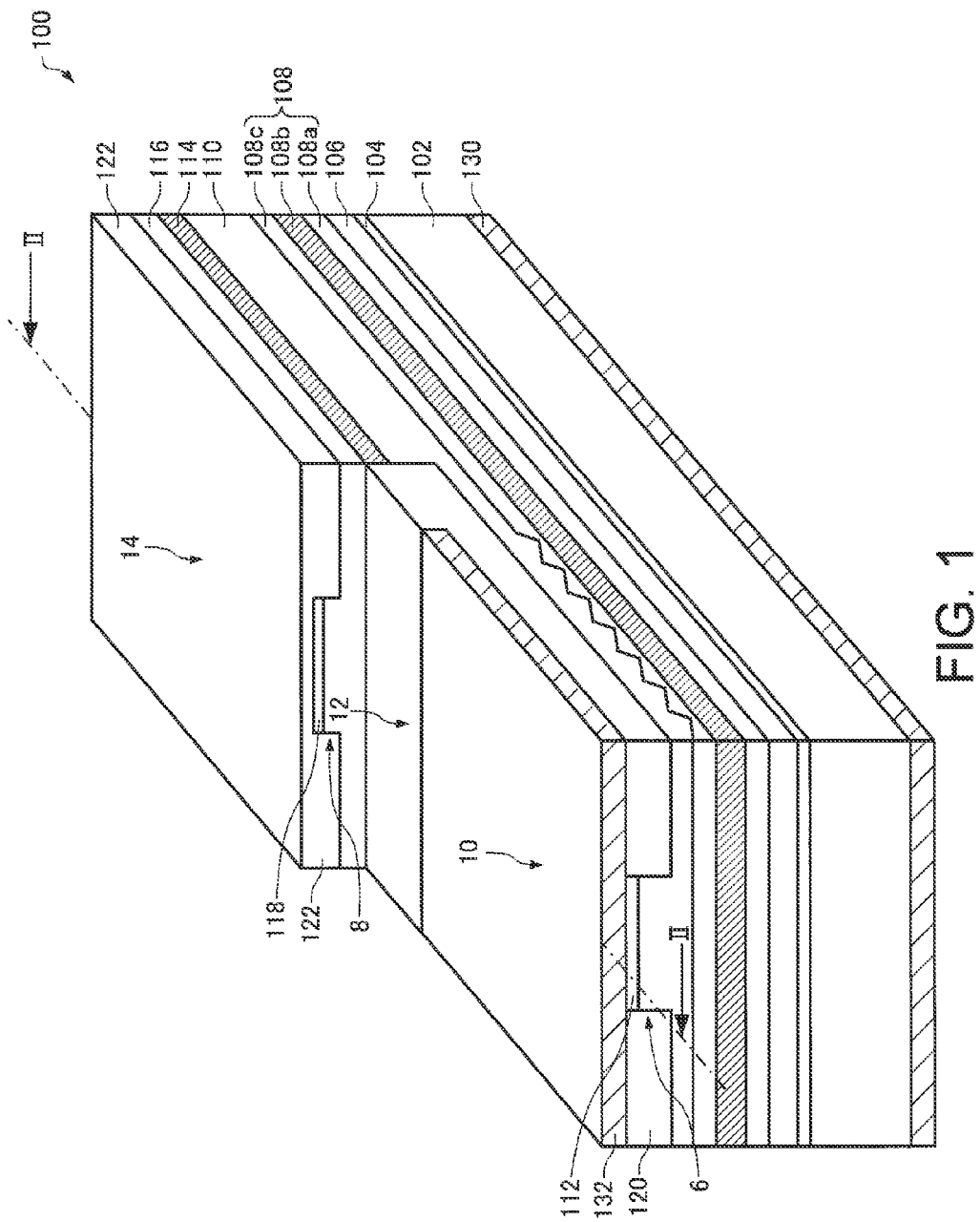
FIG. 1 is a perspective view schematically illustrating a short optical pulse generator according to a first embodiment.
Figure 2:
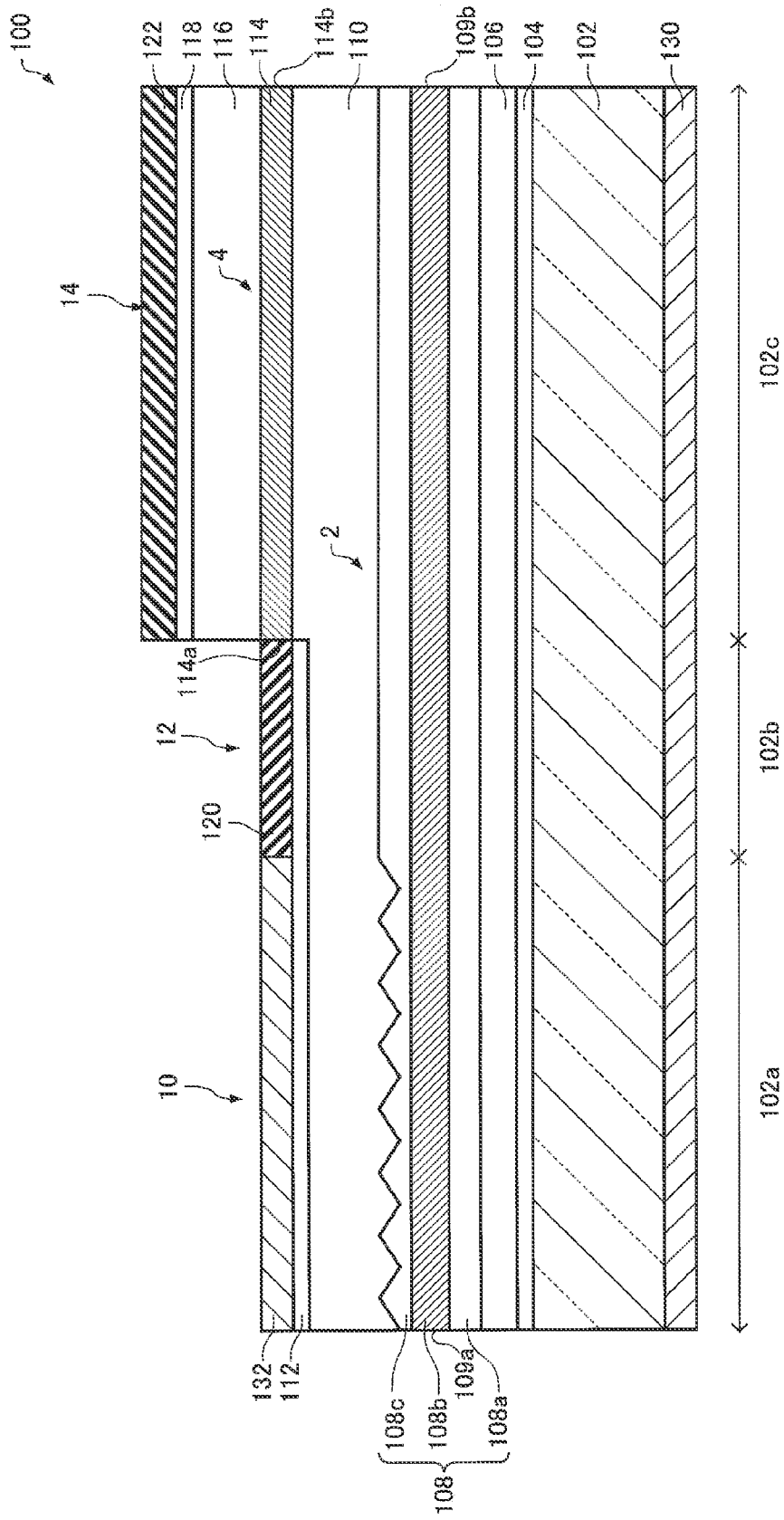
FIG. 2 is a cross-sectional view schematically illustrating the short optical pulse generator according to the first embodiment.

First, a short optical pulse generator 100 according to a first embodiment will be described with reference to the drawings. FIG. 1 is a perspective view schematically illustrating the short optical pulse generator 100 according to the present embodiment. FIG. 2 is a cross-sectional view schematically illustrating the short optical pulse generator 100 according to the present embodiment, and is a cross-sectional view taken along the line II-II of FIG. 1.

The short optical pulse generator 100 includes, as shown in FIGS. 1 and 2, an optical pulse generation portion 10 which generates an optical pulse, a frequency chirp portion 12 which gives a frequency chirp to the optical pulse, and a group velocity dispersion portion 14 which causes a group velocity difference corresponding to a wavelength in the optical pulse given the frequency chirp.

The optical pulse generation portion 10 generates an optical pulse. Here, the optical pulse is a light which varies in intensity rapidly in a short time. A pulse width (full width at half maximum FWHM) of an optical pulse generated by the optical pulse generation portion 10 is not particularly limited, and is, for example, 1 picosecond (ps) or more and 100 ps or less. The optical pulse generation portion 10 is a semiconductor laser having, for example, a quantum well structure (a first core layer 108), and is a distributed feedback (DFB) laser in the example shown in FIG. 1. In addition, the optical pulse generation portion 10 may be a semiconductor laser such as, for example, a DBR laser or a mode locked laser. Further, the optical pulse generation portion 10 is not limited to a semiconductor laser, and may be, for example, a super luminescent diode (SLD). The optical pulse generated by optical pulse generation portion 10 propagates through an optical waveguide 2 including a first clad layer 106, a first core layer 108, and a second clad layer 110.

The frequency chirp portion 12 applies a frequency chirp to the optical pulse generated by the optical pulse generation portion 10. The frequency chirp portion 12 is made of, for example, a semiconductor material, and has a quantum well structure. In the shown example, the frequency chirp portion 12 has the first core layer 108 with a quantum well structure. When the optical pulse propagates through the optical waveguide 2 of the frequency chirp portion 12, a refractive index of an optical waveguide material changes due to an optical Kerr effect, and thereby a phase of an electric field changes (self phase modulation effect). A frequency chirp is applied to the optical pulse due to this self phase modulation effect. Here, the frequency chirp indicates a phenomenon in which a frequency of an optical pulse varies with time.

Since the frequency chirp portion 12 is made of a semiconductor material, the frequency chirp portion has a low response speed to an optical pulse having a pulse width of about 1 ps to 100 ps. For this reason, the frequency chirp portion 12 applies the optical pulse a frequency chirp (up chirp or down chirp) which is proportional to the intensity (the square of the electric field amplitude) of the optical pulse (that is, the frequency of the optical pulse).

Here, the up chirp corresponds to a case where a frequency of the optical pulse increases with time, and the down chirp corresponds to a case where a frequency of the optical pulse decreases with time. In other words, the up chirp indicates situation where a wavelength of the optical pulse is shortened with time, and the down chirp indicates situation where a wavelength of the optical pulse is lengthened with time.

The group velocity dispersion portion 14 causes a group velocity difference corresponding to a wavelength (frequency) in the optical pulse given the frequency chirp. Specifically, the group velocity dispersion portion 14 can cause a group velocity difference in the optical pulse given the frequency chirp such that a pulse width of the optical pulse decreases (pulse compression). For example, the group velocity dispersion portion 14 causes negative group velocity dispersion (abnormal dispersion) in an up-chirped optical pulse so as to reduce a pulse width. In this case, the group velocity dispersion portion 14 is an abnormal dispersion medium. Here, the abnormal dispersion indicates that a group velocity is reduced according to an increase in wavelength.

In addition, the group velocity dispersion portion 14 causes positive group velocity dispersion in a down-chirped optical pulse so as to reduce a pulse width. In this case, the group velocity dispersion portion 14 is a normal dispersion medium. Here, the normal dispersion indicates that a group velocity increases according to an increase in wavelength. As above, the group velocity dispersion portion 14 performs pulse compression based on the group velocity dispersion. A pulse width of the optical pulse compressed by the group velocity dispersion portion 14 is not particularly limited, and is, for example, 1 femtosecond (fs) or more and 800 fs or less.

The group velocity dispersion portion 14 has two optical waveguides 2 and 4 which are disposed in a mode coupling distance. In other words, the two optical waveguides 2 and 4 form a so-called coupled waveguide. In addition, the mode coupling distance is a distance in which light beams which propagate through the optical waveguide 2 and the optical waveguide 4 can mutually be sent and received. The group velocity dispersion portion 14 can cause a large group velocity difference due to mode coupling in the two optical waveguides 2 and 4. In addition, the group velocity dispersion portion 14 may have normal dispersion or abnormal dispersion in a wavelength range of the optical pulse.

Next, a structure of the short optical pulse generator 100 will be described. In the short optical pulse generator 100, as shown in FIGS. 1 and 2, the optical pulse generation portion 10, the frequency chirp portion 12, and the group velocity dispersion portion 14 are integrally formed. In other words, in the short optical pulse generator 100, the optical pulse generation portion 10, the frequency chirp portion 12, and the group velocity dispersion portion 14 are provided on the same substrate 102.

Specifically, the short optical pulse generator 100 includes, the substrate 102, a buffer layer 104, the first clad layer 106, the first core layer 108, the second clad layer 110, a cap layer 112, a second core layer 114, a third clad layer 116, a cap layer 118, insulating layers 120 and 122, a first electrode 130, and a second electrode 132.

The substrate 102 is, for example, a first conductivity type (for example, an n type) GaAs substrate. The substrate 102 includes a first region 102a where the optical pulse generation portion 10 is formed, a second region 102b where the frequency chirp portion 12 is formed, and a third region 102c where the group velocity dispersion portion 14 is formed.

The buffer layer 104 is provided on the substrate 102. The buffer layer 104 is, for example, an n type GaAs layer. The buffer layer 104 can improve crystallinity of a layer formed thereon.

The first clad layer 106 is provided on the buffer layer 104. The first clad layer 106 is, for example, an n type AlGaAs layer.

A first guide layer 108a is provided on the first clad layer 106. The first guide layer 108a is, for example, an i type AlGaAs layer.

An MQW layer 108b is provided on the first guide layer 108a. The MQW layer 108b has a multi-quantum well structure in which three quantum well structures each of which is formed by, for example, a GaAs well layer and an AlGaAs barrier layer which overlap each other. In the shown example, the number of quantum wells of the MQW layer 108b (the number of laminated GaAs well layers and AlGaAs barrier layers) is the same on the upper sides of the first to third regions 102a to 102c. In other words, the number of quantum wells of the MQW layer 108b is the same in the respective portions 10, 12 and 14. Further, the number of quantum wells of the MQW layer 108b on the upper side of the first region 102a, the number of quantum wells of the MQW layer 108b on the upper side of the second region 102b, and the number of quantum wells of the MQW layer 108b on the upper side of the third region 102c may be different from each other. That is, the number of quantum wells of the MQW layer 108b forming the optical pulse generation portion 10, the number of quantum wells of the MQW layer 108b forming the frequency chirp portion 12, and the number of quantum wells of the MQW layer 108b forming the group velocity dispersion portion 14 may be different from each other. In addition, the quantum well structure indicates a general quantum well structure in a semiconductor light emitting device field, and is a structure in which two or more types of materials having different band gaps are used, and a thin film (mm order) of a material having a smaller band gap is formed between thin films of a material having a larger band gap.

A second guide layer 108c is provided on the MQW layer 108b. The second guide layer 108c is, for example, an i type AlGaAs layer. A periodic structure forming a DFB type resonator is provided in the second guide layer 108c. The periodic structure is provided on the upper side of the first region 102a. The periodic structure is formed by two layers 108c and 110 with different refractive indexes as shown in FIG. 2.

The first core layer 108 through which light (optical pulse) occurring in the MQW layer 108b propagates can be formed by the first guide layer 108a, the MQW layer 108b, and the second guide layer 108c. The first guide layer 108a and the second guide layer 108c confine injection carriers (electrons and holes) in the MQW layer 108b and also confine light in the first core layer 108.

The second clad layer 110 is provided on the first core layer 108. The second clad layer 110 is, for example, a second conductivity type (for example, a p type) AlGaAs layer.

In the shown example, the optical waveguide 2 is formed by the first clad layer 106, the first core layer 108, and the second clad layer 110. The optical waveguide 2 extends from an end surface 109a of the first core layer 108 to an end surface 109b of the first core layer 108 on an opposite side thereto. The optical waveguide 2 is provided linearly in the shown example.

In addition, the first core layer 108 may have a quantum well structure on the upper side of the first region 102a and the second region 102b. For example, the first core layer 108 may not have a quantum well structure on the upper side of the third region 102c. In other words, the first core layer 108 forming the group velocity dispersion portion 14 may not have a quantum well structure. In this case, the first core layer 108 is a single layer of, for example, an AlGaAs layer.

In the optical pulse generation portion 10, a pin diode is formed by, for example, the p type second clad layer 110, the first core layer 108 which is not doped with impurities, and the n type first clad layer 106. Each layer of the first clad layer 106 and the second clad layer 110 has a larger band gap and a smaller refractive index than the first core layer 108. The first core layer 108 has a function to generate light, and amplify and guide the light. The first clad layer 106 and the second clad layer 110 have a function to confine injection carriers (electrons and holes) and light (a function to suppress light leakage) with the first core layer 108 interposed therebetween.

In the optical pulse generation portion 10, when a forward bias voltage of the pin diode is applied between the first electrode 130 and the second electrode 132, recombination of electrons and holes occurs in the first core layer 108 (the MQW layer 108b). Light is emitted by the recombination. Linked stimulated emission occurs with the generated light (optical pulse) as the starting point, and the intensity of the light (optical pulse) is amplified in the optical waveguide 2.

The buffer layer 104, the first clad layer 106, the first core layer 108, and the second clad layer 110 are provided over the first region 102a, the second region 102b, and the third region 102c of the substrate 102. In other words, these layers 104, 106, 108 and 110 are layers common to the optical pulse generation portion 10, the frequency chirp portion 12, and the group velocity dispersion portion 14, and are continuous layers. The optical waveguide 2 is formed by the first clad layer 106, the first core layer 108, and the second clad layer 110, which are continuously located in the optical pulse generation portion 10, the frequency chirp portion 12, and the group velocity dispersion portion 14.

The cap layer 112 is provided on the second clad layer 110. More specifically, the cap layer 112 is provided on the second clad layer 110 and the upper side of the first region 102a and the second region 102b of the substrate 102. The cap layer 112 may have ohmic contact with the second electrode 132. The cap layer 112 is, for example, a p type GaAs layer.

The cap layer 112, and a part of the second clad layer 110 provided on the upper side of the first region 102a and the second region 102b form a columnar section 6. For example, in the optical pulse generation portion 10, a current path between the electrodes 130 and 132 is determined depending on a planar shape which is viewed from a laminate direction of each layer of the columnar section 6.

The insulating layer 120 is provided on the second clad layer 110 and on the lateral side of the columnar section 6 as shown in FIG. 1. In addition, the insulating layer 120 is provided on the cap layer 112 on the upper side of the second region 102b. The insulating layer 120 is, for example, a SiN layer, a $SiO_2$ layer, a SiON layer, an $Al_2O_3$ layer, a polyimide layer, or the like.

In a case where the above-described materials are used as the insulating layer 120, a current between the electrodes 130 and 132 can avoid the insulating layer 120 and flow through the columnar section 6 interposed between the insulating layers 120. In addition, the insulating layer 120 may have a refractive index smaller than a refractive index of the second clad layer 110. In this case, an effective refractive index of the vertical cross-section of the part forming the insulating layer 120 is smaller than an effective refractive index of the vertical cross-section of the part which does not form the insulating layer 120, that is, the part forming the columnar section 6. Thus, light can be confined in the optical waveguide 2 in the planar direction with high efficiency. Further, although not shown, not the above-described materials but an air layer may be used as the insulating layer 120. In this case, an air layer can function as the insulating layer 120.

The first electrode 130 is provided on the entire lower surface of the substrate 102. The first electrode 130 comes into contact with a layer (the substrate 102 in the shown example) which has ohmic contact with the first electrode 130. The first electrode 130 is electrically connected to the first clad layer 106 via the substrate 102. The first electrode 130 is one electrode for driving the optical pulse generation portion 10. The first electrode 130 may use an electrode or the like formed by laminating, for example, a Cr layer, a AuGe layer, a Ni layer, and a Au layer in this order from the substrate 102 side. In addition, the first electrode 130 may be provided only on the lower side of the first region 102a of the substrate 102.

The second electrode 132 is provided on the upper surface of the cap layer 112 and the upper side of the first region 102a. In addition, the second electrode 132 may be provided on the insulating layer 120. The second electrode 132 is electrically connected to the second clad layer 110 via the cap layer 112. The second electrode 132 is the other electrode for driving the optical pulse generation portion 10. The second electrode 132 may use an electrode or the like formed by laminating, for example, a Cr layer, a AuZn layer, and a Au layer in this order from the cap layer 112 side. In addition, in the shown example, a double-side electrode structure is employed in which the first electrode 130 is provided on the lower surface side of the substrate 102 and the second electrode 132 is provided on the upper surface side of the substrate 102; however, a single-side electrode structure may be employed in which the first electrode 130 and the second electrode 132 are provided on the same surface side (for example, the upper surface side) of the substrate 102.

The second core layer 114 is provided on the second clad layer 110. More specifically, the second core layer 114 is provided on the second clad layer 110 and the upper side of the third region 102c. The second core layer 114 is, for example, an i type AlGaAs layer. The second core layer 114 is interposed between the second clad layer 110 and the third clad layer 116.

The third clad layer 116 is provided on the second core layer 114. The third clad layer 116 is, for example, an n type AlGaAs layer.

In the shown example, the optical waveguide 4 is formed by the second clad layer 110, the second core layer 114, and the third clad layer 116. The optical waveguide 4 extends from an end surface 114a of the second core layer 114 to an end surface 114b of the second core layer 114 on an opposite side thereto. In the shown example, the optical waveguide 4 is provided linearly.

The optical waveguide 2 and the optical waveguide 4 are disposed in a mode coupling distance. In other words, the optical waveguide 2 and the optical waveguide 4 form a coupled waveguide. The optical waveguide 2 and the optical waveguide 4 are arranged in the laminate direction of the semiconductor layers 104 to 118 forming the group velocity dispersion portion 14. In the shown example, the optical waveguide 4 is disposed on the upper side of the optical waveguide 2, and thus the optical waveguide 2 overlaps the optical waveguide 4 when viewed from the laminate direction of the semiconductor layers 104 to 118.

The cap layer 118 is provided on the third clad layer 116. The cap layer 118 is, for example, an n type GaAs layer. The cap layer 118 and a part of the third clad layer 116 form a columnar section 8.

As shown in FIG. 1, the insulating layer 122 is provided on the third clad layer 116 and the lateral side of the columnar section 8. Further, the insulating layer 122 is provided on the cap layer 118. The insulating layer 122 is, for example, a SiN layer, a $SiO_2$ layer, a SiON layer, an $Al_2O_3$ layer, a polyimide layer, or the like.

The insulating layer 122 may have a refractive index smaller than a refractive index of the third clad layer 116. In this case, an effective refractive index of the vertical cross-section of the part forming the insulating layer 122 is smaller than an effective refractive index of the vertical cross-section of the part which does not form the insulating layer 122, that is, the part forming the columnar section 8. Thus, light can be confined in the optical waveguide 2 and the optical waveguide 4 in the planar direction with high efficiency. Further, although not shown, not the above-described materials but an air layer may be used as the insulating layer 122. In this case, an air layer can function as the insulating layer 122.

As above, although a description has been made of a case of using an AlGaAs based semiconductor material as an example of the short optical pulse generator 100 according to the present embodiment, a material thereof is not limited thereto, and may use, for example, other semiconductor materials such as, AlGaN based, GaN based, InGaN based, GaAs based, InGaAs based, InGaAsP based, and ZnCdSe based materials.

Further, although not shown, an electrode for applying a reverse bias to the frequency chirp portion 12 may be provided. Thus, an absorption characteristic of the frequency chirp portion 12 can be controlled so as to adjust a chirp value of a frequency. In addition, an electrode for applying a voltage to the group velocity dispersion portion 14 may be provided. For example, in the group velocity dispersion portion 14, a voltage can be applied to the optical waveguide 2 by providing an electrode electrically connected to the first clad layer 106 and an electrode electrically connected to the second clad layer 110. Further, a voltage can be applied to the optical waveguide 4 by providing an electrode electrically connected to the second clad layer 110 and an electrode electrically connected to the third clad layer 116. Furthermore, a voltage can be applied to the optical waveguide 2 and the optical waveguide 4 by providing an electrode electrically connected to the first clad layer 106 and an electrode electrically connected to the third clad layer 116. Thus, it is possible to control a group velocity dispersion amount of the group velocity dispersion portion 14. In other words, a disparity between group velocity dispersion values caused by a device manufacturing disparity can be corrected so as to be adjusted to a group velocity dispersion value which is optimal for controlling a short optical pulse width.

Figure 3:
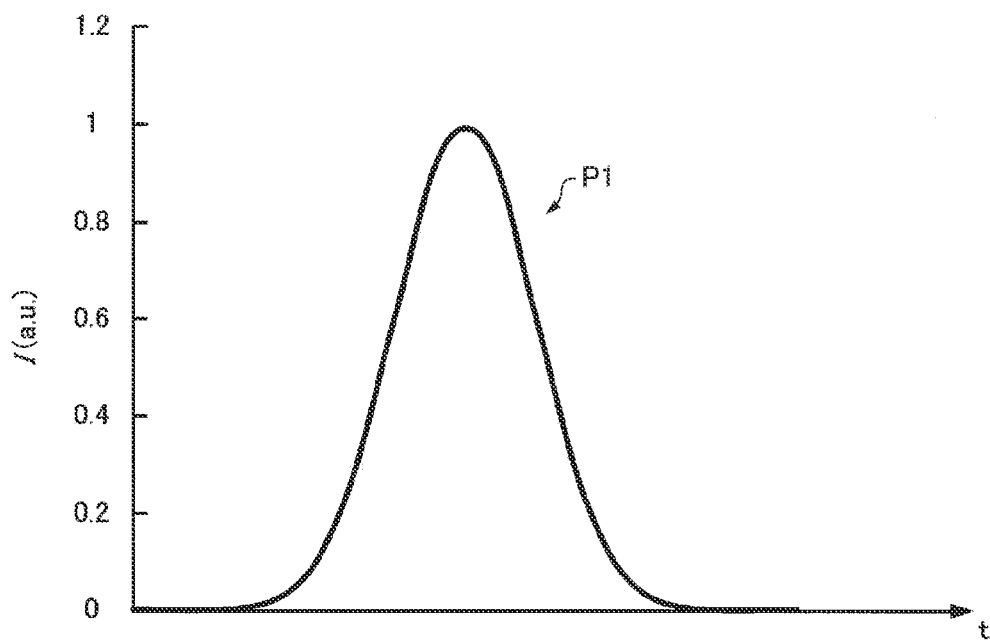
FIG. 3 is a graph illustrating an example of an optical pulse generated by an optical pulse generation portion.
Figure 4:
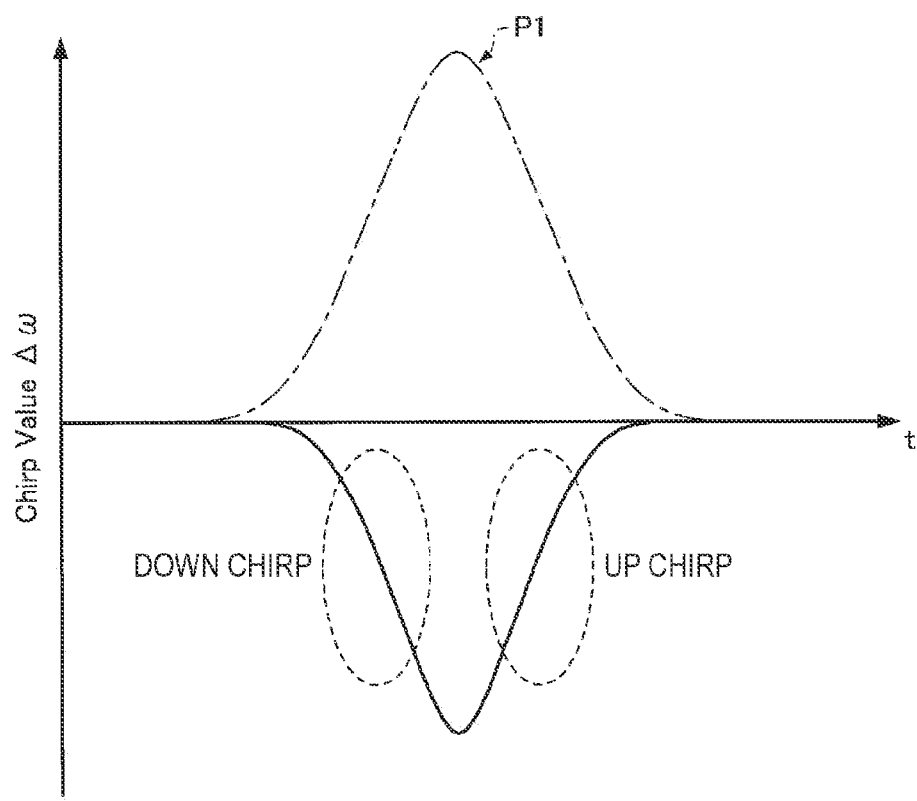
FIG. 4 is a graph illustrating an example of a chirp characteristic of a frequency chirp portion.
Figure 5:
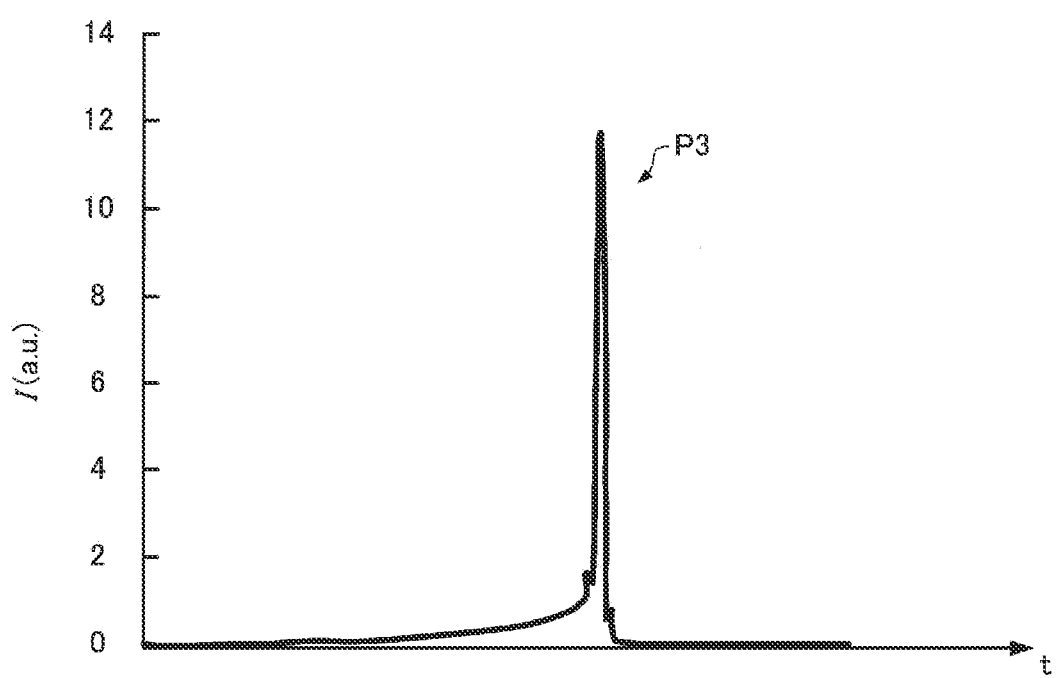
FIG. 5 is a graph illustrating an example of an optical pulse generated by a group velocity dispersion portion.

Next, an operation of the short optical pulse generator 100 will be described. FIG. 3 is a graph illustrating an example of an optical pulse P1 generated by the optical pulse generation portion 10. In the graph shown in FIG. 3, the transverse axis t expresses time, and the longitudinal axis I expresses a light intensity (the square of the electric field amplitude). FIG. 4 is a graph illustrating an example of a chirp characteristic of the frequency chirp portion 12. In the graph shown in FIG. 4, the transverse axis t expresses time, and the longitudinal axis $\Delta\omega$ expresses a chirp value (a frequency variation amount). In addition, in FIG. 4, the optical pulse P1 is indicated by the dot chain line, and a chirp value $\Delta\omega$ corresponding to the optical pulse P1 is indicated by the solid line. FIG. 5 is a graph illustrating an example of an optical pulse P3 generated by the group velocity dispersion portion 14. In the graph shown in FIG. 5, the transverse axis t expresses time, and the longitudinal axis I expresses a light intensity. In addition, the graph shown in FIG. 5 corresponds to the graph shown in FIG. 3.

The optical pulse generation portion 10 generates, for example, the optical pulse P1 shown in FIG. 3. In the optical pulse generation portion 10, a forward bias voltage of the pin diode is applied between the first electrode 130 and the second electrode 132 so as to generate the optical pulse P1. The optical pulse P1 has a Gauss waveform in the shown example. A pulse width (full width at half maximum FWHM) t of the optical pulse P1 is 10 ps (picoseconds) in the shown example. The optical pulse P1 propagates through the optical waveguide 2 and is incident to the frequency chirp portion 12.

The frequency chirp portion 12 has a chirp characteristic proportional to the light intensity. The following Equation (1) is an equation representing an effect of the frequency chirp.

$$\Delta\omega = -\frac{n_2 l \omega_0}{2c\tau_r}|E|^2 \quad (1)$$

Here, $\Delta\omega$ indicates a chirp value (frequency variation amount), c indicates the light velocity, $\tau_r$ indicates response time of a nonlinear refractive index effect, $n_2$ indicates a nonlinear refractive index, l indicates a waveguide length, $\omega_0$ indicates a center frequency, and E indicates the amplitude of an electric field.

The frequency chirp portion 12 applies the frequency chirp expressed by Equation (1) to the optical pulse P1 which propagates through the optical waveguide 2. Specifically, as shown in FIG. 4, the frequency chirp portion 12 decreases a frequency with time at the front part of the optical pulse P1 and increases a frequency with time at the rear part of the optical pulse P1 for the optical pulse P1. In other words, the frequency chirp portion 12 applies a down chirp to the front part of the optical pulse P1 and applies an up chirp to the rear part of the optical pulse P1. Therefore, the optical pulse P1 generated by the optical pulse generation portion 10 passes through the frequency chirp portion 12 and becomes an optical pulse (hereinafter, referred to as an "optical pulse P2") of which the front part is down-chirped and the rear part is up-chirped. The optical pulse P2 (not shown) applied the chirp is incident to the group velocity dispersion portion 14.

The group velocity dispersion portion 14 causes (group velocity dispersion) a group velocity difference corresponding to a wavelength (frequency) in the optical pulse P2 given the frequency chirp so as to perform pulse compression. In the group velocity dispersion portion 14, the optical pulse P2 passes through the coupled waveguide formed by the optical waveguides 2 and 4, thereby causing the group velocity difference in the optical pulse P2. In the example of FIG. 5, the group velocity dispersion portion 14 causes negative group velocity dispersion in the optical pulse P2 so as to compress the rear part of the up-chirped optical pulse P2. Thus, the optical pulse P3 is generated. In the shown example, the pulse width t of the optical pulse P3 is 0.33 ps. The optical pulse P3 is emitted from at least one of the end surface 109b of the optical waveguide 2 and the end surface 114b of the optical waveguide 4.

The short optical pulse generator 100 according to the present embodiment has, for example, the following features.

The short optical pulse generator 100 includes the optical pulse generation portion 10 which has a quantum well structure and generates an optical pulse, the frequency chirp portion 12 which has a quantum well structure and chirps a frequency of the optical pulse, a plurality of optical waveguides 2 and 4 disposed in a mode coupling distance, and the group velocity dispersion portion 14 which causes a group velocity difference corresponding to a wavelength in the chirped optical pulse. Thus, an optical pulse generated by the optical pulse generation portion 10 can be compressed (a pulse width thereof is reduced) so as to emit an optical pulse (short optical pulse) with a pulse width of, for example, 1 fs or more and 800 fs or less.

In addition, according to the short optical pulse generator 100, since the frequency chirp portion 12 has a quantum well structure, it is possible to miniaturize the device. The reason that this reduction in size is possible will be described more fully below.

As expressed by the above-described Equation (1), the chirp value $\Delta\omega$ is proportional to the nonlinear refractive index $n_2$. In other words, the larger the nonlinear refractive index, the greater the chirp value per unit length. Here, a nonlinear refractive index $n_2$ of a normal quartz optical fiber ($SiO_2$ glass) is approximately $10^{-20}$ m²/W. In contrast, a nonlinear refractive index $n_2$ of a semiconductor material with a quantum well structure is approximately $10^{-10}$ to $10^{-8}$ m²/W. As above, the semiconductor material with a quantum well structure has a considerably larger nonlinear refractive index $n_2$ than the quartz optical fiber. For this reason, by using the semiconductor material with a quantum well structure as the frequency chirp portion 12, it is possible to increase a chirp value per unit length and to thus reduce a length of an optical waveguide for giving a frequency chirp as compared with a case of using the quartz optical fiber. Therefore, it is possible to reduce the size of the frequency chirp portion 12 and to thereby reduce the size of the overall device.

In addition, in the short optical pulse generator 100, since the group velocity dispersion portion 14 has two optical waveguides 2 and 4 disposed in a mode coupling distance, it is possible to cause a great group velocity difference in an optical pulse through mode coupling. Therefore, it is possible to reduce a length of the optical waveguide for causing a group velocity difference and to thereby decrease the size of a device.

In the short optical pulse generator 100, the group velocity dispersion portion 14 is made of semiconductor materials (the semiconductor layers 106, 108, 110, 114 and 116), and thus it is possible to easily form a coupled waveguide (the optical waveguides 2 and 4) as compared with, for example, a quartz optical fiber.

In the short optical pulse generator 100, the optical pulse generation portion 10, the frequency chirp portion 12, and the group velocity dispersion portion 14 are provided on the same substrate 102. For this reason, it is possible to efficiently form a semiconductor layer forming the optical pulse generation portion 10, a semiconductor layer forming the frequency chirp portion 12, and a semiconductor layer forming the group velocity dispersion portion 14 in the same process by using epitaxial growth or the like. In addition, it is possible to easily perform alignment between the optical pulse generation portion 10 and the frequency chirp portion 12 and alignment between the frequency chirp portion 12 and the group velocity dispersion portion 14.

In the short optical pulse generator 100, the layer (the first core layer 108) with a quantum well structure of the optical pulse generation portion 10 and the layer (the first core layer 108) with a quantum well structure of the frequency chirp portion 12 are the same layer and are continuously located. In addition, in the short optical pulse generator 100, the layer (the first core layer 108) with a quantum well structure of the frequency chirp portion 12 and the core layer (the first core layer 108) forming at least one of a plurality of optical waveguides 2 and 4 of the group velocity dispersion portion 14 comprise the same layer and are continuously located. Thus, it is possible to reduce an optical loss between the optical pulse generation portion 10 and the frequency chirp portion 12 and optical loss between the frequency chirp portion 12 and the group velocity dispersion portion 14. For example, in configurations where the layer with a quantum well structure of the optical pulse generation portion 10 and the layer with a quantum well structure of the frequency chirp portion 12 are not continuously positioned, that is, when there is a space or an optical element between these layers, an optical loss may occur during the period when an optical pulse is emitted from the optical pulse generation portion 10 and is incident to the frequency chirp portion 12. In addition, this is also the same for a case where the layer with quantum well structure of the frequency chirp portion 12 and the core layer forming at least one of a plurality of optical waveguides 2 and 4 of the group velocity dispersion portion 14 are not continuously positioned.

In the short optical pulse generator 100, the group velocity dispersion portion 14 includes a plurality of laminated semiconductor layers 106, 108, 110, 114 and 116, and a plurality of optical waveguides 2 and 4, which are arranged in the laminate direction of the semiconductor layers. Thus, a distance between the optical waveguides 2 and 4 can be controlled using a film thickness of the semiconductor layer. Therefore, it is possible to control a distance between the optical waveguides 2 and 4 with high accuracy. Further, for example, the first core layer 108 forming the optical waveguide 2 and the second core layer 114 forming the optical waveguide 4 may be made from different materials.

1.2 Manufacturing Method of Short Optical Pulse Generator

Figure 6:
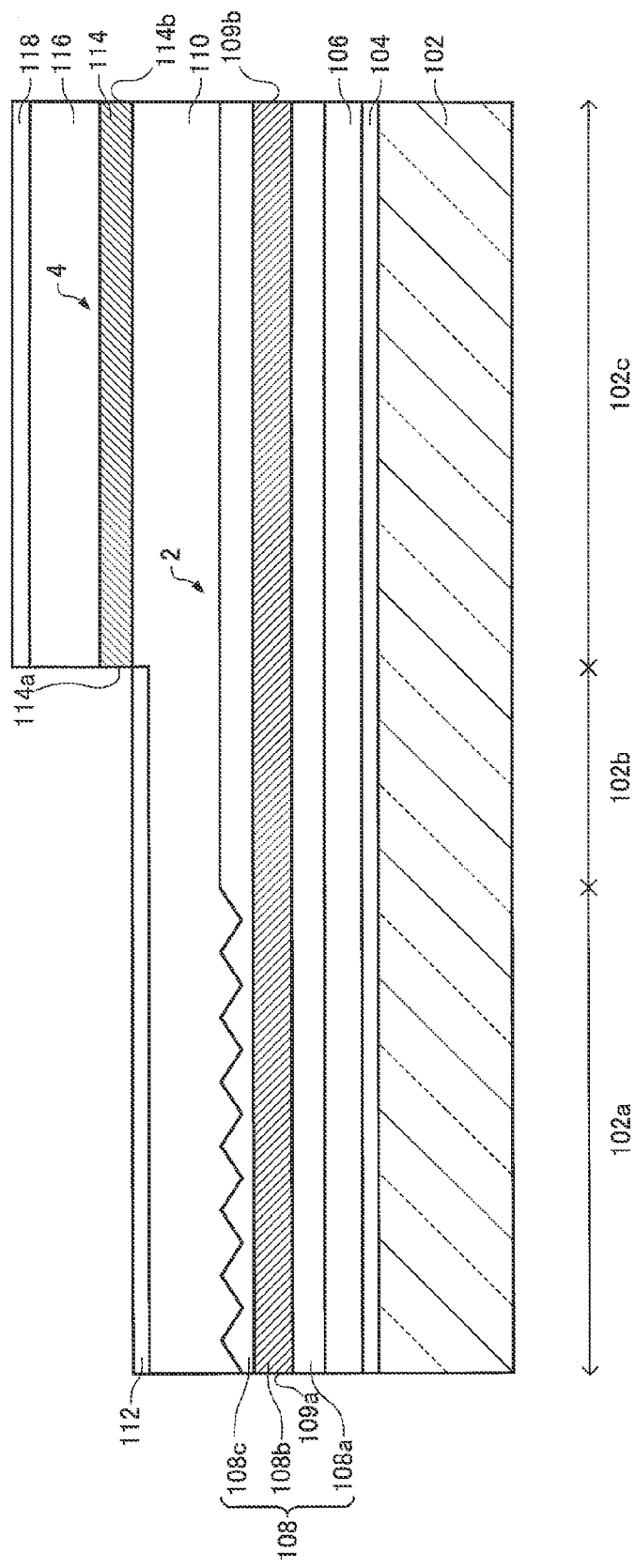
FIG. 6 is a cross-sectional view schematically illustrating manufacturing steps of the short optical pulse generator according to the first embodiment.
Figure 7:
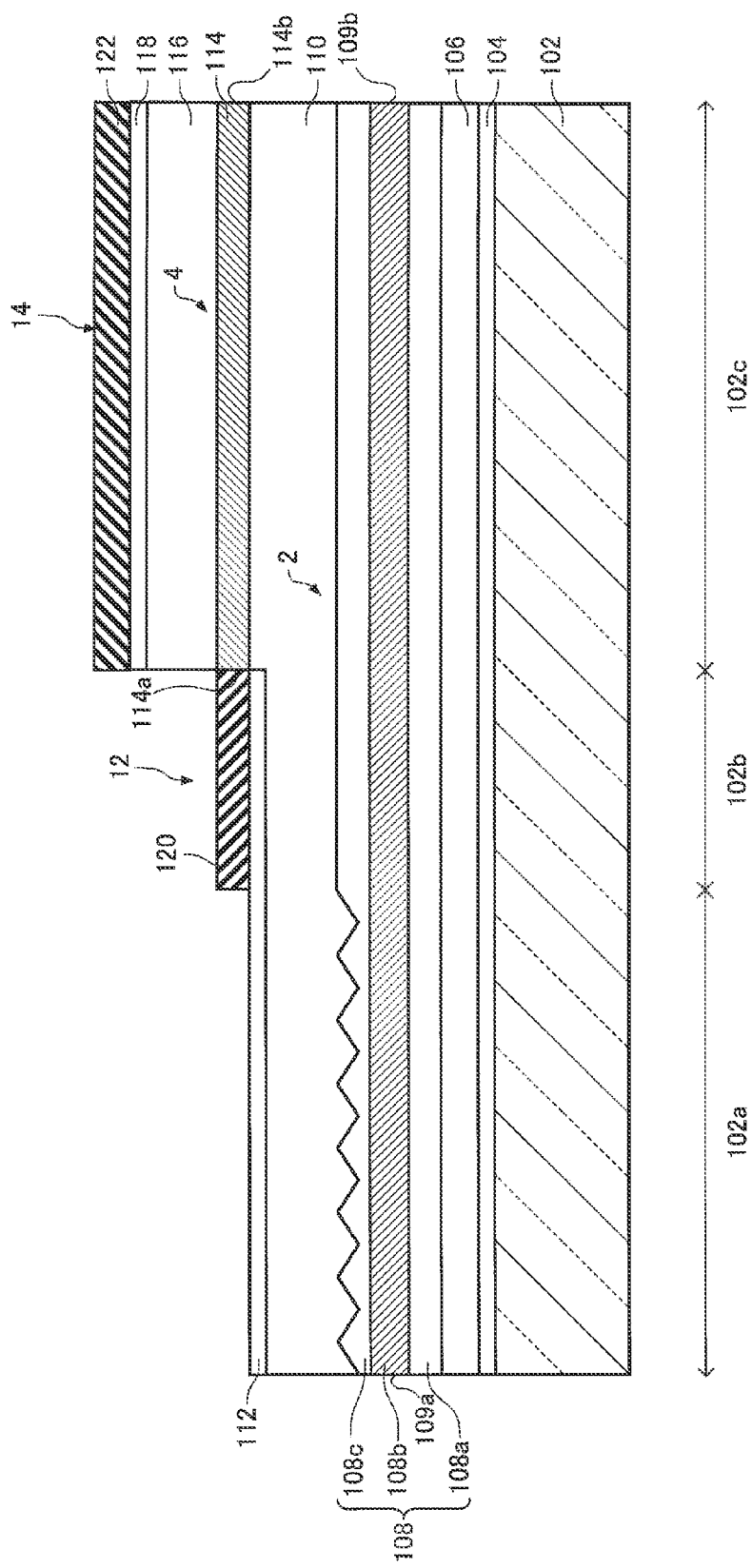
FIG. 7 is a cross-sectional view schematically illustrating manufacturing steps of the short optical pulse generator according to the first embodiment.

Next, a manufacturing method of the short optical pulse generator according to the present embodiment will be described with reference to the drawings. FIGS. 6 and 7 are cross-sectional views schematically illustrating manufacturing steps of the short optical pulse generator 100 according to the present embodiment.

As shown in FIG. 6, the buffer layer 104, the first clad layer 106, the first core layer 108, the second clad layer 110, the second core layer 114, the cap layer 112, the third clad layer 116, and the cap layer 118 are epitaxially grown in this order on the substrate 102. For example, a metal organic chemical vapor deposition (MOCVD) method, a molecular beam epitaxy (MBE) method, and the like may be used as methods of epitaxial growth. In addition, if the first core layer 108 is to be formed, first, the first guide layer 108a and the MQW layer 108b are grown on the first clad layer 106. Next, the second guide layer 108c is grown on the MQW layer 108b. Further, the upper surface of the second guide layer 108c on the upper side of the first region 102a undergoes interference exposure and is etched so as to form an uneven surface. Thereafter, the second clad layer 110 with a different refractive index is grown on the second guide layer 108c including the uneven surface. Thus, a periodic structure is formed in the second guide layer 108c. In this way, the first core layer 108 is formed.

Next, the cap layer 118 and the third clad layer 116 are etched so as to form the columnar section 8. Successively, the cap layer 118, the third clad layer 116, and the second core layer 114 on the upper sides of the first region 102a and the second region 102b of the substrate 102 are removed, and the cap layer 112 and the second clad layer 110 are etched, thereby forming the columnar section 6 (refer to FIG. 1).

As shown in FIG. 7, the insulating layers 120 and 122 are formed on the columnar sections 6 and 8 and on lateral sides of the columnar sections 6 and 8 (refer to FIG. 1). The insulating layer 120 is not formed on the columnar section 6 of the upper side of the first region 102a. The insulating layers 120 and 122 are formed using, for example, a CVD method, a coating method, or the like.

As shown in FIGS. 1 and 2, the second electrode 132 is formed on the columnar section 6 (the cap layer 112). The second electrode is formed on the cap layer 112 by forming a film using a vacuum deposition method. Next, the first electrode 130 is formed on the lower surface of the substrate 102. The first electrode 130 is formed using, for example, a vacuum deposition method. In addition, an order of the first electrode 130 and the second electrode 132 to be formed is not particularly limited.

Through above-described steps, the short optical pulse generator 100 can be manufactured.

According to the manufacturing method of the short optical pulse generator 100, it is possible to obtain the short optical pulse generator 100 with a reduced size.

1.3 Modification Examples of Short Optical Pulse Generator

Next, a short optical pulse generator related to modification examples of the present embodiment will be described with reference to the drawings. In the short optical pulse generator related to the modification examples of the present embodiment described below, a member having the same function as the constituent member of the above-described short optical pulse generator 100 is given the same reference numeral, and detailed description thereof will be omitted.

1. Modification Example 1

Figure 8:
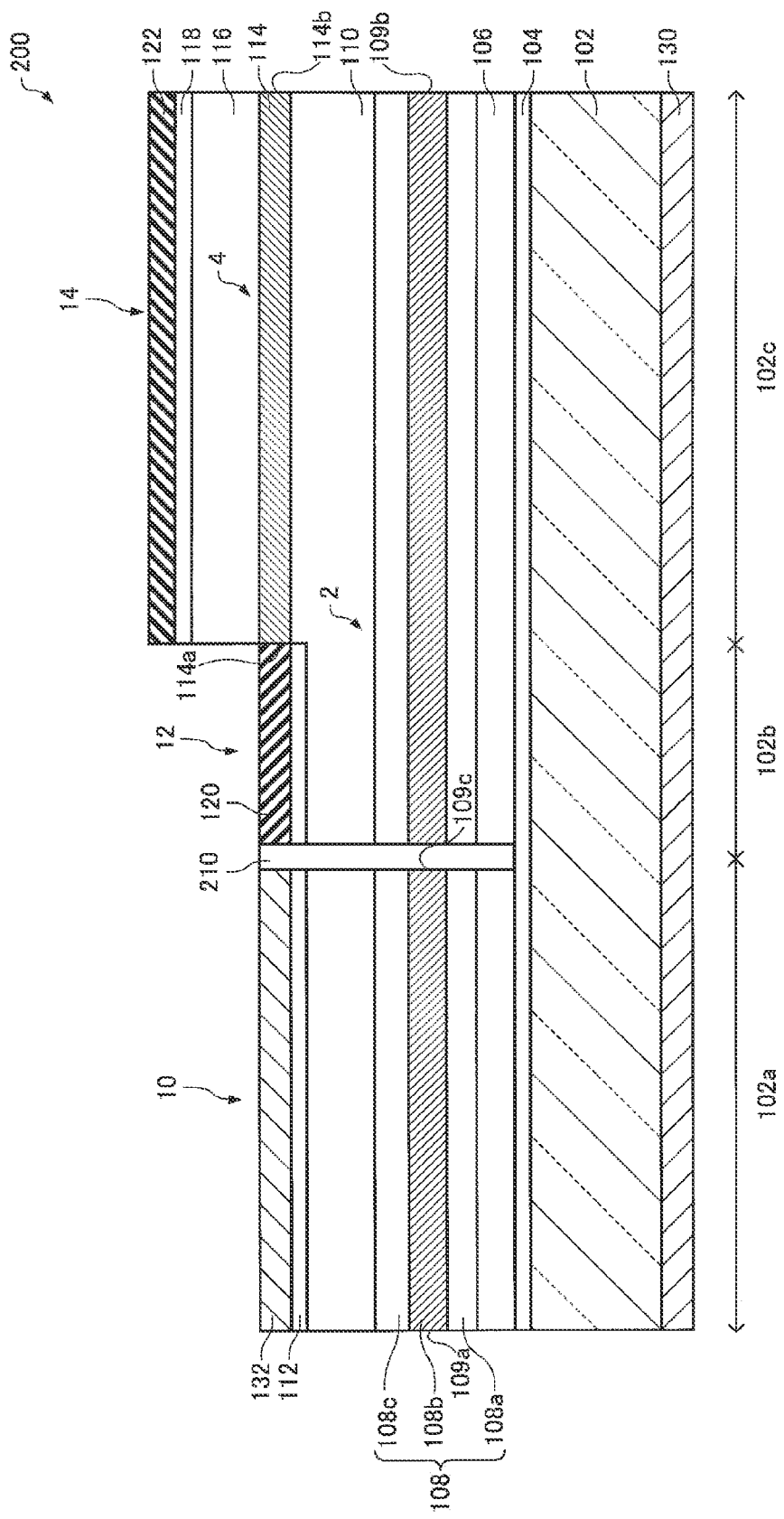
FIG. 8 is a cross-sectional view schematically illustrating a short optical pulse generator related to Modification Example 1 of the first embodiment.

First, Modification Example 1 will be described. FIG. 8 is a cross-sectional view schematically illustrating a short optical pulse generator 200 related to Modification Example 1.

In the above-described short optical pulse generator 100, as shown in FIG. 2, the optical pulse generation portion 10 is a DFB laser.

In contrast, in the short optical pulse generator 200, as shown in FIG. 8, the optical pulse generation portion 10 is a Fabry-Perot type semiconductor laser.

In the short optical pulse generator 200, a groove 210 is provided at the boundary between the first region 102a and the second region 102b in plan view (when viewed from the laminate direction of the semiconductor layers 104 to 118). The groove 210 is provided so as to penetrate through the cap layer 112, the second clad layer 110, the first core layer 108, and the first clad layer 106. The groove 210 is provided, and thereby an end surface 109c is provided in the first core layer 108. In the optical pulse generation portion 10, the end surface 109a and the end surface 109c function as a reflective surface so as to form a Fabry-Perot resonator. An optical pulse emitted from the end surface 109c of the optical pulse generation portion 10 passes through the groove 210 and is incident to the frequency chirp portion 12.

2. Modification Example 2

Figure 9:
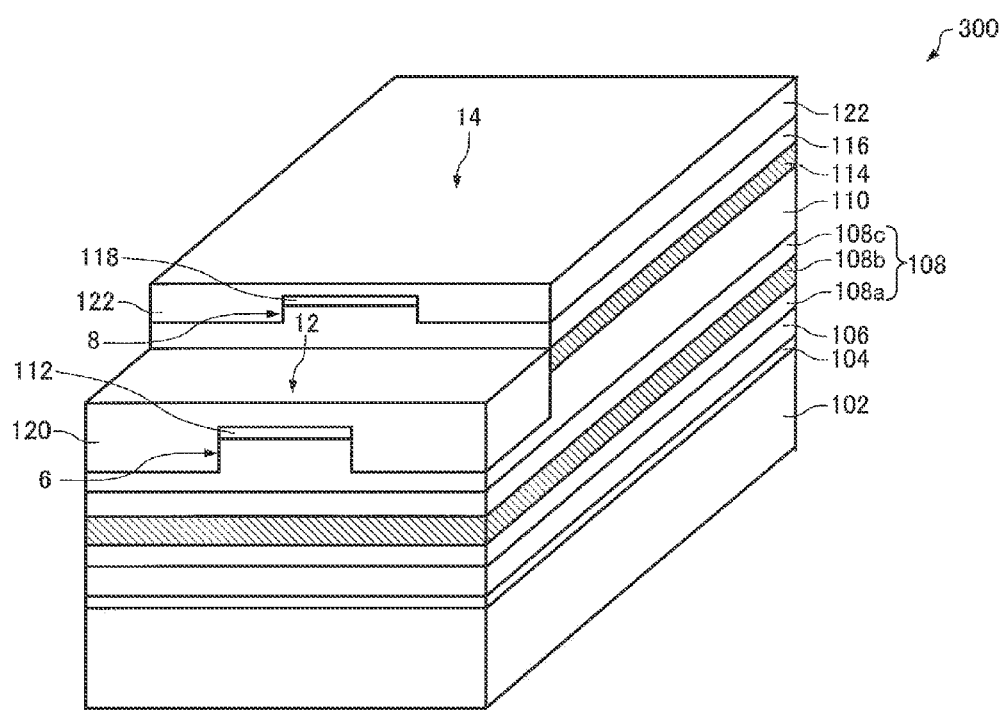
FIG. 9 is a perspective view schematically illustrating a short optical pulse generator related to Modification Example 2 of the first embodiment.
Figure 10:
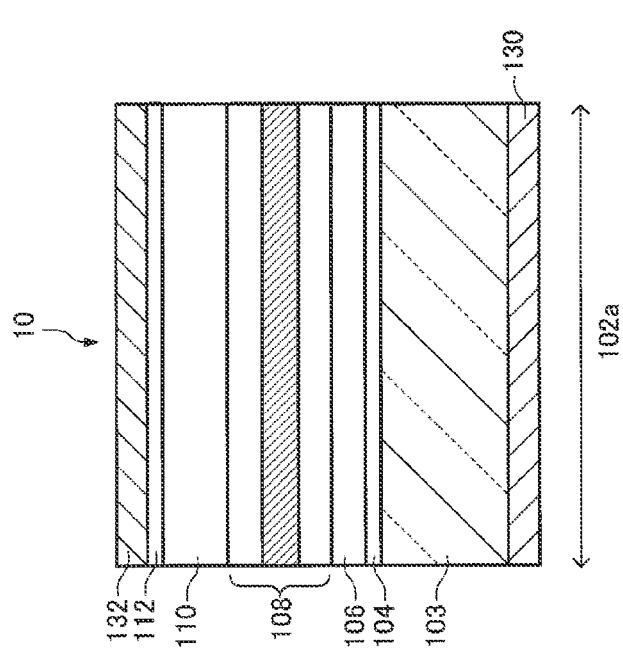
FIG. 10 is a cross-sectional view schematically illustrating the short optical pulse generator related to Modification Example 2 of the first embodiment.
Figure 10:
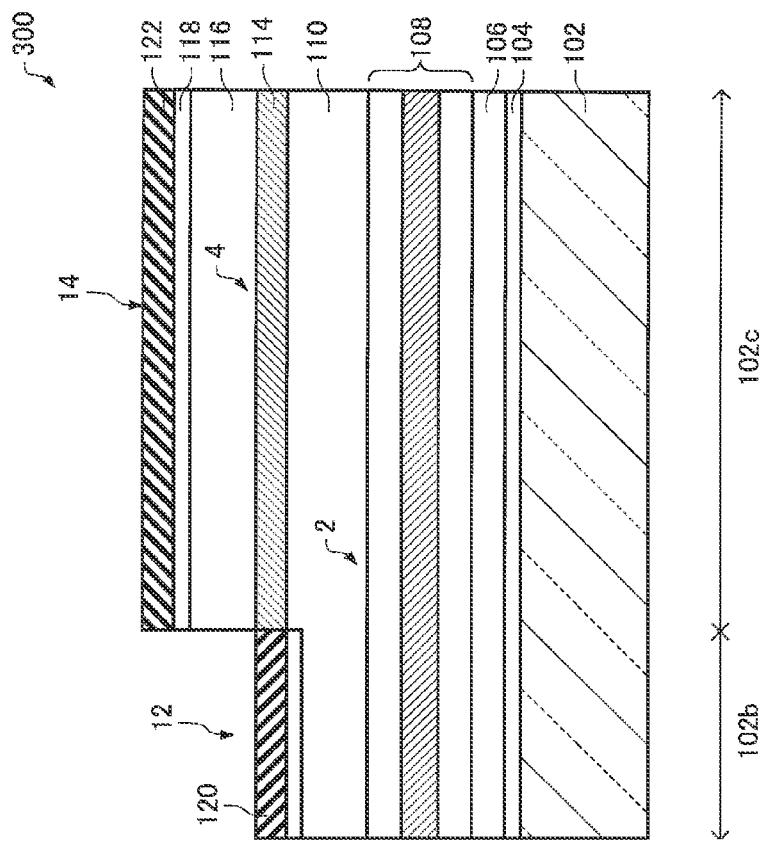

Next, Modification Example 2 will be described. FIG. 9 is a perspective view schematically illustrating a short optical pulse generator 300 related to Modification Example 2. FIG. 10 is a cross-sectional view schematically illustrating the short optical pulse generator 300 related to Modification Example 2. In addition, in FIG. 9, for convenience, the optical pulse generation portion 10 and the optical element 310 are not shown. Further, FIG. 10 corresponds to FIG. 2.

In the above-described short optical pulse generator 100, as shown in FIGS. 1 and 2, the optical pulse generation portion 10, the frequency chirp portion 12, and the group velocity dispersion portion 14 are integrally provided.

In contrast, in the short optical pulse generator 300, as shown in FIGS. 9 and 10, the frequency chirp portion 12 and the group velocity dispersion portion 14 are integrally provided. In other words, in the short optical pulse generator 300, the frequency chirp portion 12 and the group velocity dispersion portion 14 are provided on the same substrate 102.

The optical pulse generation portion 10 is provided on a substrate 103 which is different from the substrate 102 on which the frequency chirp portion 12 and the group velocity dispersion portion 14 are provided. A configuration of the optical pulse generation portion 10 is not particularly limited as long as it can emit an optical pulse. In the shown example, the optical pulse generation portion 10 is a Fabry-Perot type semiconductor laser. The optical element 310 is disposed between the optical pulse generation portion 10 and the frequency chirp portion 12. The optical element 310 is a lens for allowing an optical pulse emitted from the optical pulse generation portion 10 to be incident to the frequency chirp portion 12. In addition, the optical element 310 may not be provided, and an optical pulse emitted from the optical pulse generation portion 10 may be directly incident to the frequency chirp portion 12.

According to the short optical pulse generator 300, the frequency chirp portion 12 and the group velocity dispersion portion 14 are provided on the same substrate 102, and thus it is possible to efficiently form the semiconductor layer forming the frequency chirp portion 12 and the semiconductor layer forming the group velocity dispersion portion 14 in the same process by using epitaxial growth or the like. In addition, it is possible to easily perform alignment between the frequency chirp portion 12 and the group velocity dispersion portion 14. Further, since the layer with a quantum well structure of the frequency chirp portion 12 and the core layer of the group velocity dispersion portion 14 are continuously located, it is possible to reduce an optical loss between the frequency chirp portion 12 and the group velocity dispersion portion 14.

3. Modification Example 3

Figure 11:
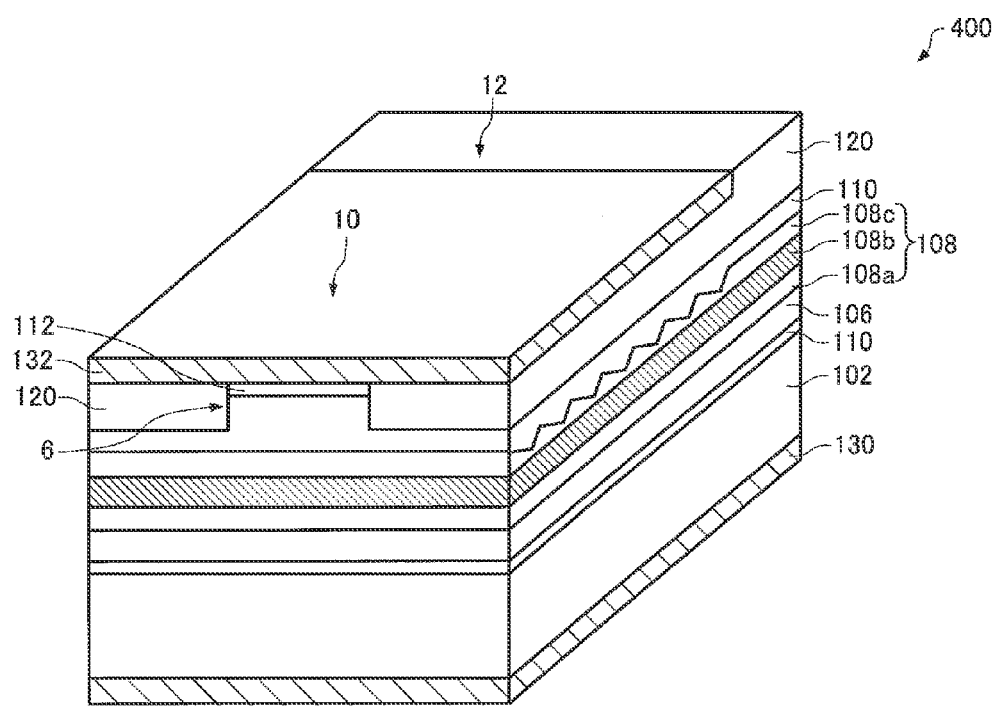
FIG. 11 is a perspective view schematically illustrating a short optical pulse generator related to Modification Example 3 of the first embodiment.
Figure 12:
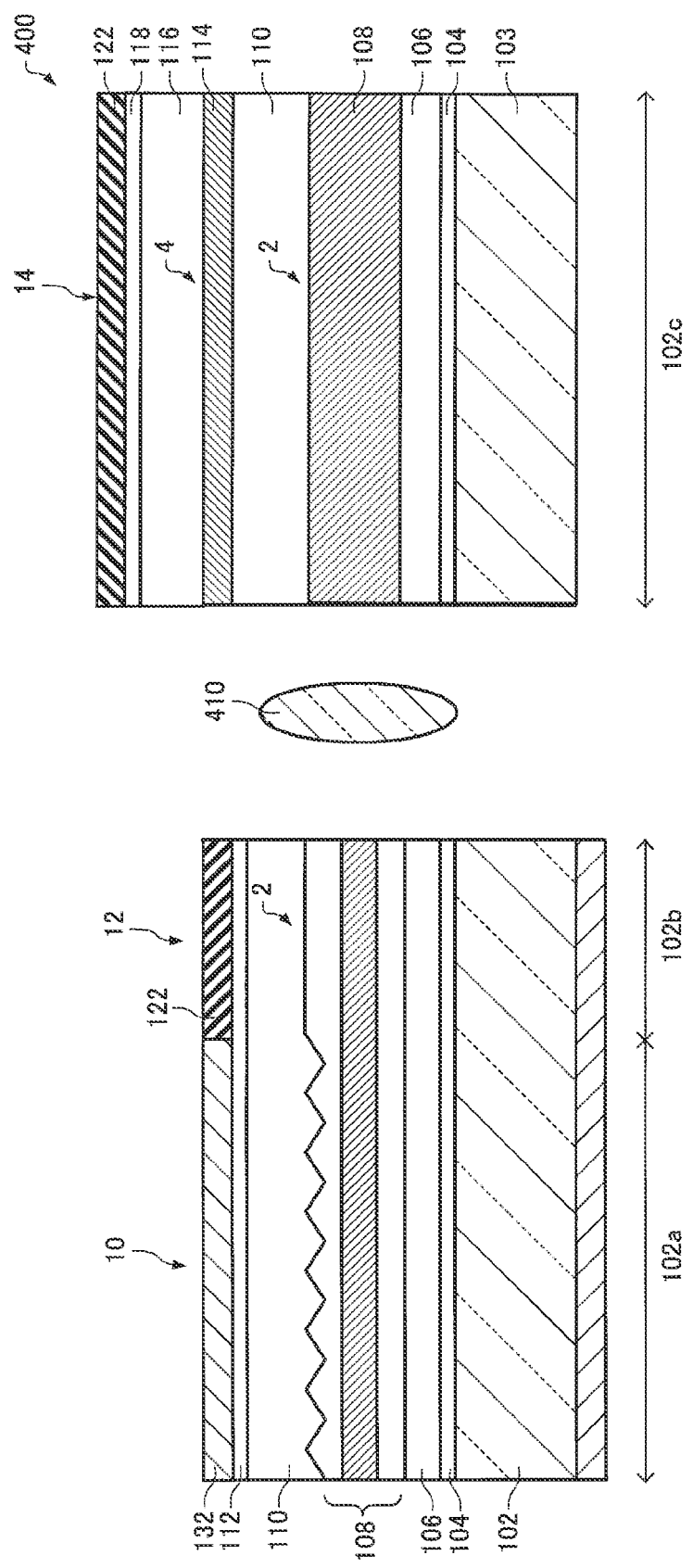
FIG. 12 is a cross-sectional view schematically illustrating the short optical pulse generator related to Modification Example 3 of the first embodiment.

Next, Modification Example 3 will be described. FIG. 11 is a perspective view schematically illustrating a short optical pulse generator 400 related to Modification Example 3. FIG. 12 is a cross-sectional view schematically illustrating the short optical pulse generator 400 related to Modification Example 3. In addition, in FIG. 11, for convenience, the group velocity dispersion portion 14 and the optical element 410 are not shown. Further, FIG. 12 corresponds to FIG. 2.

In the above-described short optical pulse generator 100, as shown in FIGS. 1 and 2, the optical pulse generation portion 10, the frequency chirp portion 12, and the group velocity dispersion portion 14 are integrally formed.

In contrast, in the short optical pulse generator 400, as shown in FIGS. 11 and 12, the optical pulse generation portion 10 and the frequency chirp portion 12 are integrally provided. In other words, in the short optical pulse generator 400, the optical pulse generation portion 10 and the frequency chirp portion 12 are provided on the same substrate 102.

The group velocity dispersion portion 14 is provided on a substrate 103 which is different from the substrate 102 on which the optical pulse generation portion 10 and the frequency chirp portion 12 are provided. The first core layer 108 of the group velocity dispersion portion 14 may not have a quantum well structure. The first core layer 108 is, for example, a single-layer AlGaAs layer. In addition, a composition of the first core layer 108 may be different from a composition of the second core layer 114. For example, the first core layer 108 may be an $Al_{0.35}Ga_{0.65}As$ layer, and the second core layer 114 may be an $Al_{0.23}Ga_{0.77}As$ layer.

A layer structure (band structure) of the semiconductor layers 104, 106, 108, 110, 114, 116 and 118 forming the group velocity dispersion portion 14 is not particularly limited. For example, all the semiconductor layers 104 to 118 may be n type (or p type) semiconductor layers. In addition, for example, the first clad layer 106 may be of an n type, the first core layer 108 may be of an i type, the second clad layer 110 may be of a p type, the second core layer 114 may be of an i type, and the third clad layer 116 may be of a p type. In this case, a voltage can be applied to the semiconductor layers forming the optical waveguide 2 by providing an electrode connected to the first clad layer 106 and an electrode connected to the second clad layer 110. Further, for example, the first clad layer 106 may be of an n type, the first core layer 108 may be of an i type, the second clad layer 110 may be of an n type, the second core layer 114 may be of an i type, and the third clad layer 116 may be of a p type. In this case, a voltage can be applied to the semiconductor layers forming the optical waveguide 4 by providing an electrode connected to the second clad layer 110 and an electrode connected to the third clad layer 116. Furthermore, for example, the first clad layer 106 may be of an n type, the first core layer 108 may be of an i type, the second clad layer 110 may be of a p type, the second core layer 114 may be of an i type, and the third clad layer 116 may be of an n type. In this case, a voltage can be applied to the semiconductor layers forming the optical waveguide 2 and the optical waveguide 4 by providing an electrode connected to the first clad layer 106 and an electrode connected to the third clad layer 116. In this way, a voltage is applied to the semiconductor layers forming the optical waveguides 2 and 4, and thus a refractive index varies due to a nonlinear optical effect, thereby changing the propagation constant. Thus, since a group velocity dispersion value varies, it is possible to correct a disparity between group velocity dispersion values caused by a device disparity.

The optical element 410 is disposed between the frequency chirp portion 12 and the group velocity dispersion portion 14. The optical element 410 is a lens for allowing an optical pulse emitted from the frequency chirp portion 12 to be incident to the group velocity dispersion portion 14. In addition, the optical element 410 may not be provided, and an optical pulse emitted from the frequency chirp portion 12 may be directly incident to the group velocity dispersion portion 14.

According to the short optical pulse generator 400, the optical pulse generation portion 10 and the frequency chirp portion 12 are provided on the same substrate 102, and thus it is possible to efficiently form the semiconductor layer forming the optical pulse generation portion 10 and the semiconductor layer forming the frequency chirp portion 12 in the same process. In addition, it is possible to easily perform alignment between the optical pulse generation portion 10 and the frequency chirp portion 12. Further, since the layer with a quantum well structure of the optical pulse generation portion 10 and the layer with a quantum well structure of the frequency chirp portion 12 are continuously located, it is possible to reduce an optical loss between the optical pulse generation portion 10 and the frequency chirp portion 12.

4. Modification Example 4

Figure 13:
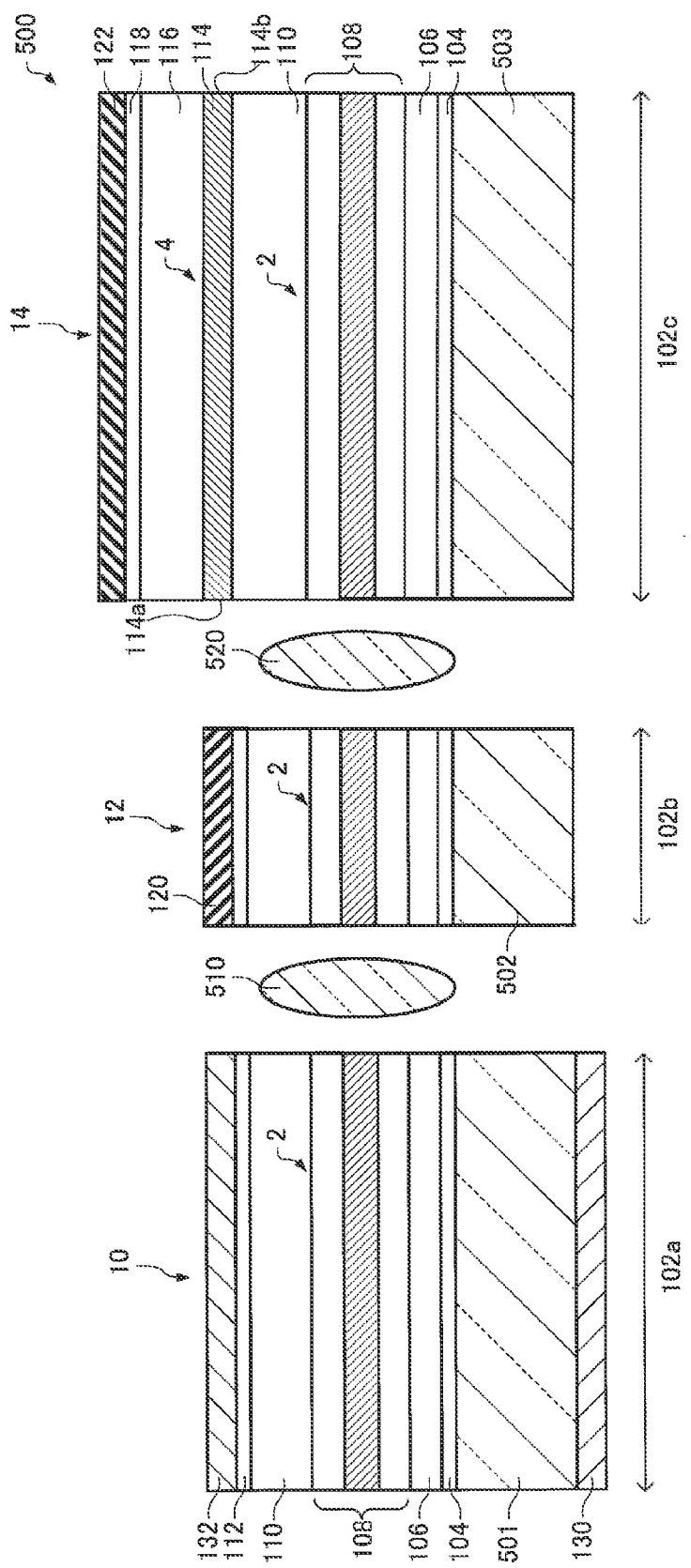
FIG. 13 is a cross-sectional view schematically illustrating a short optical pulse generator related to Modification Example 4 of the first embodiment.

Next, Modification Example 4 will be described. FIG. 13 is a cross-sectional view schematically illustrating a short optical pulse generator 500 related to Modification Example 4. Further, FIG. 13 corresponds to FIG. 2.

In the above-described short optical pulse generator 100, as shown in FIGS. 1 and 2, the optical pulse generation portion 10, the frequency chirp portion 12, and the group velocity dispersion portion 14 are integrally formed.

In contrast, in the short optical pulse generator 500, as shown in FIG. 13, the optical pulse generation portion 10, the frequency chirp portion 12, and the group velocity dispersion portion 14 are formed separately from each other. In other words, in the short optical pulse generator 500, the optical pulse generation portion 10, the frequency chirp portion 12, and the group velocity dispersion portion 14 are respectively provided on different substrates 501, 502 and 503. The substrates 501, 502 and 503 may use, for example, an n type GaAs substrate, and the like.

The optical element 510 is disposed between the optical pulse generation portion 10 and the frequency chirp portion 12. The optical element 510 is a lens for allowing an optical pulse emitted from the optical pulse generation portion 10 to be incident to the frequency chirp portion 12. In addition, the optical element 520 is disposed between the frequency chirp portion 12 and the group velocity dispersion portion 14. The optical element 520 is a lens for allowing an optical pulse emitted from the frequency chirp portion 12 to be incident to the group velocity dispersion portion 14. In addition, the optical element 510 may not be provided, and an optical pulse emitted from the optical pulse generation portion 10 may be directly incident to the frequency chirp portion 12. Further, the optical element 520 may not be provided, and an optical pulse emitted from the frequency chirp portion 12 may be directly incident to the group velocity dispersion portion 14.

2. Second Embodiment

2.1 Configuration of Short Optical Pulse Generator

Figure 14:
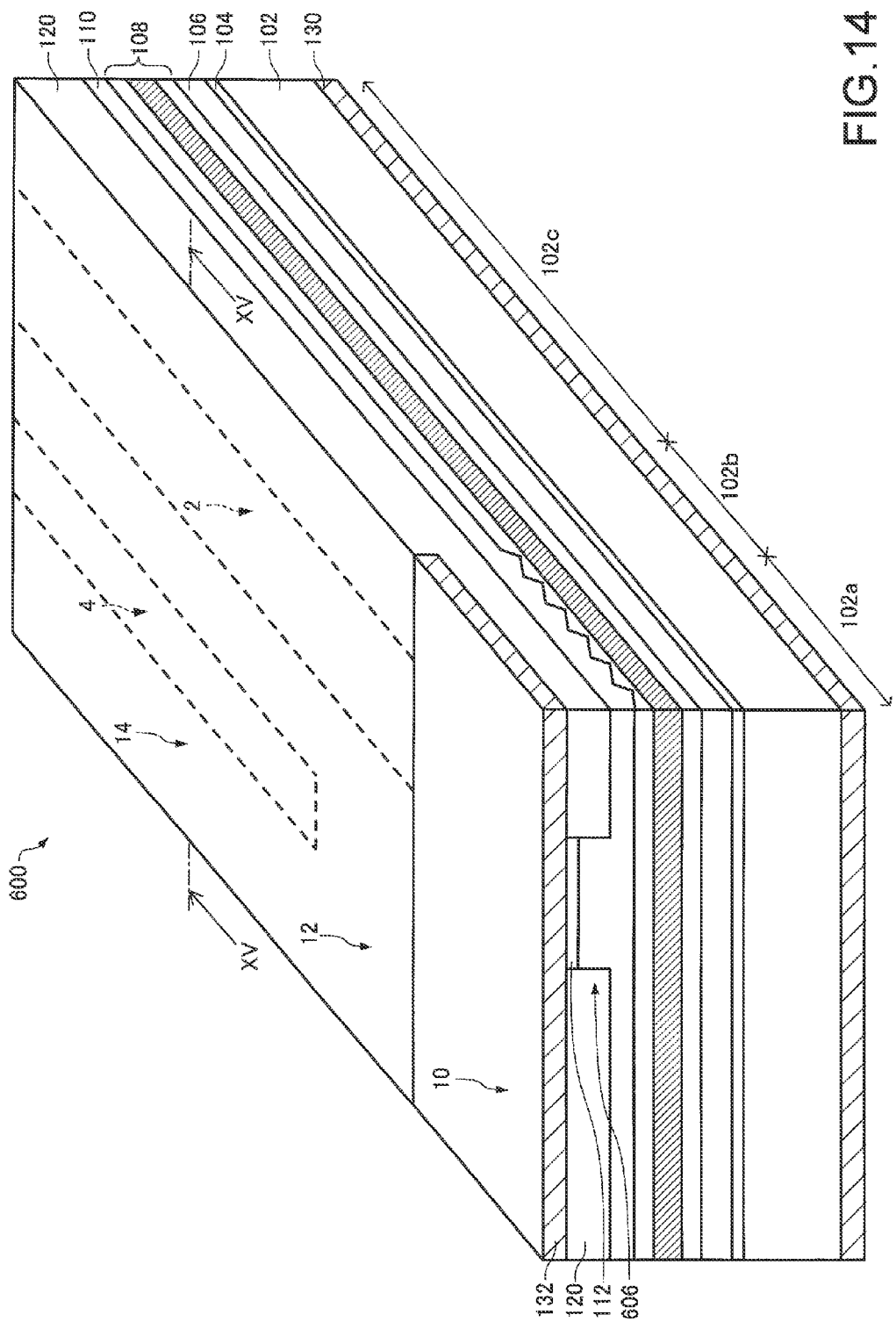
FIG. 14 is a perspective view schematically illustrating a short optical pulse generator according to a second embodiment.
Figure 15:
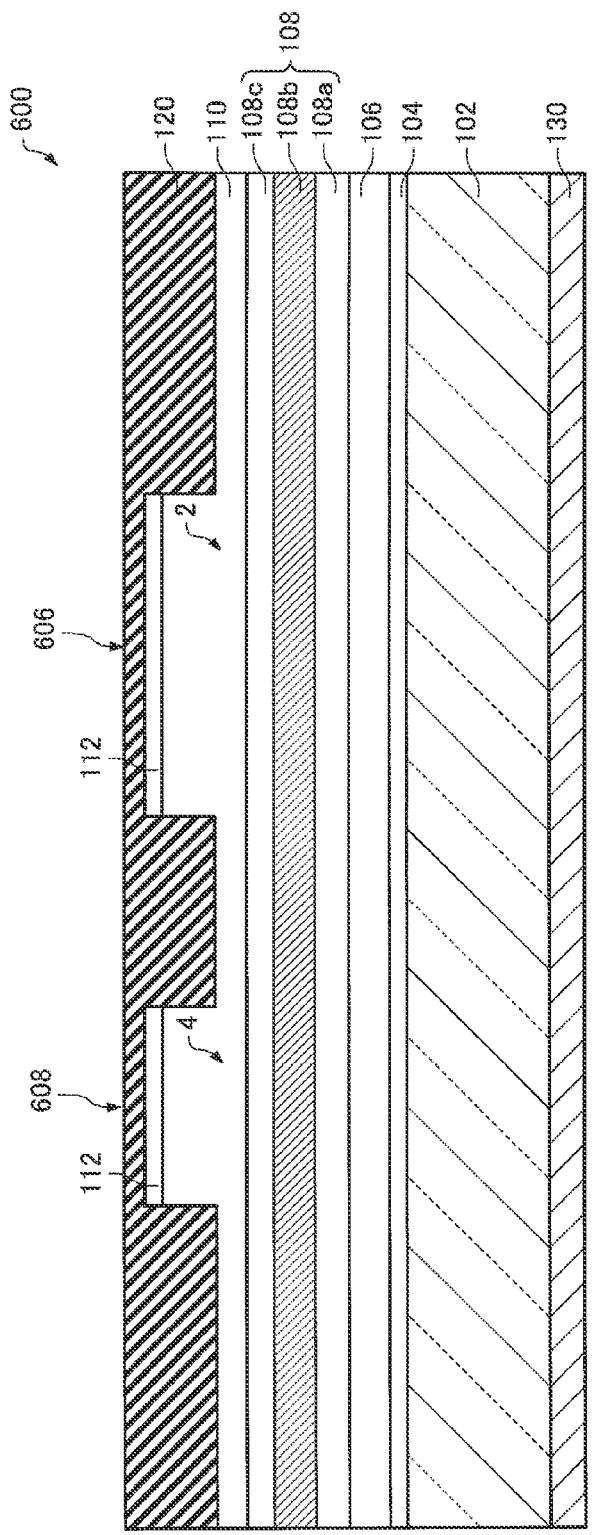
FIG. 15 is a cross-sectional view schematically illustrating the short optical pulse generator according to the second embodiment.

Next, a short optical pulse generator 600 according to a second embodiment will be described with reference to the drawings. FIG. 14 is a perspective view schematically illustrating the short optical pulse generator 600 according to the present embodiment. FIG. 15 is a cross-sectional view schematically illustrating the short optical pulse generator 600 according to the present embodiment, and is a cross-sectional view taken along the line XV-XV of FIG. 14. In the short optical pulse generator 600 according to the present embodiment described below, a member having the same function as the constituent member of the above-described short optical pulse generator 100 is given the same reference numeral, and detailed description thereof will be omitted.

In the above-described short optical pulse generator 100, as shown in FIGS. 1 and 2, the optical waveguide 2 and the optical waveguide 4 forming a coupled waveguide are disposed in the laminate direction of the semiconductor layers 104 to 118.

In contrast, in the short optical pulse generator 600, as shown in FIGS. 14 and 15, the optical waveguide 2 and the optical waveguide 4 forming a coupled waveguide are arranged in a direction perpendicular to the laminate direction of the semiconductor layers 104 to 110. In the shown example, the optical waveguides 2 and 4 are arranged in the in-surface direction of the substrate 102.

The short optical pulse generator 600 includes the substrate 102, the buffer layer 104, the first clad layer 106, the first core layer 108, the second clad layer 110, the cap layer 112, the insulating layer 120, the first electrode 130, and the second electrode 132.

The cap layer 112 and a part of the second clad layer 110 form two columnar sections 606 and 608. The columnar section 606 extends from one end surface of the first core layer 108 to the other end surface thereof. In other words, the columnar section 606 provided over the optical pulse generation portion 10, the frequency chirp portion 12, and the group velocity dispersion portion 14. The columnar section 608 is provided only on the upper side of the third region 102c of the substrate 102. In other words, the columnar section 608 is provided only in the group velocity dispersion portion 14.

The insulating layer 120 is provided on the second clad layer 110 and on the lateral sides of the columnar section 606 and the lateral sides of the columnar section 608 as shown in FIG. 15. In addition, the insulating layer 120 is provided on the columnar sections 606 and 608 and in the region other than the region where the second electrode 132 is formed. An effective refractive index of the vertical cross-section of the part forming the insulating layer 120 is smaller than an effective refractive index of the vertical cross-section of the part which does not form the insulating layer 120, that is, the part forming the columnar sections 606 and 608. Thus, light can be confined in the optical waveguides 2 and 4 in the planar direction with high efficiency. The optical waveguide 2 and the optical waveguide 4 are formed by the same semiconductor layers 106, 108 and 110.

A width (a width of the columnar section 606) of the optical waveguide 2 is different from a width (a width of the columnar section 608) of the optical waveguide 4 in the shown example. In addition, a width (a width of the columnar section 606) of the optical waveguide 2 may be the same as a width (a width of the columnar section 608) of the optical waveguide 4.

In the short optical pulse generator 600, the optical waveguides 2 and 4 forming a coupled waveguide are arranged in the direction perpendicular to the laminate direction of the semiconductor layers 104 to 110. For this reason, it is possible to reduce the number of semiconductor layers which are laminated and form the group velocity dispersion portion 14 as compared with a case where the optical waveguides 2 and 4 are arranged in the laminate direction. Therefore, it is possible to simplify manufacturing steps and to thereby reduce manufacturing costs.

In addition, although not shown, in the short optical pulse generator 600, in the same manner as in the short optical pulse generator 300 shown in FIGS. 9 and 10, the frequency chirp portion 12 and the group velocity dispersion portion 14 may be provided on the same substrate, and the optical pulse generation portion 10 may be provided on a separate substrate. Further, in the same manner as in the short optical pulse generator 400 shown in FIGS. 11 and 12, the optical pulse generation portion 10 and the frequency chirp portion 12 may be provided on the same substrate, and the group velocity dispersion portion 14 may be provided on a separate substrate. Furthermore, in the same manner as in the short optical pulse generator 500 shown in FIG. 13, the optical pulse generation portion 10, the frequency chirp portion 12, and the group velocity dispersion portion 14 may be respectively provided on separate substrates.

2.2 Manufacturing Method of Short Optical Pulse Generator

Figure 16:
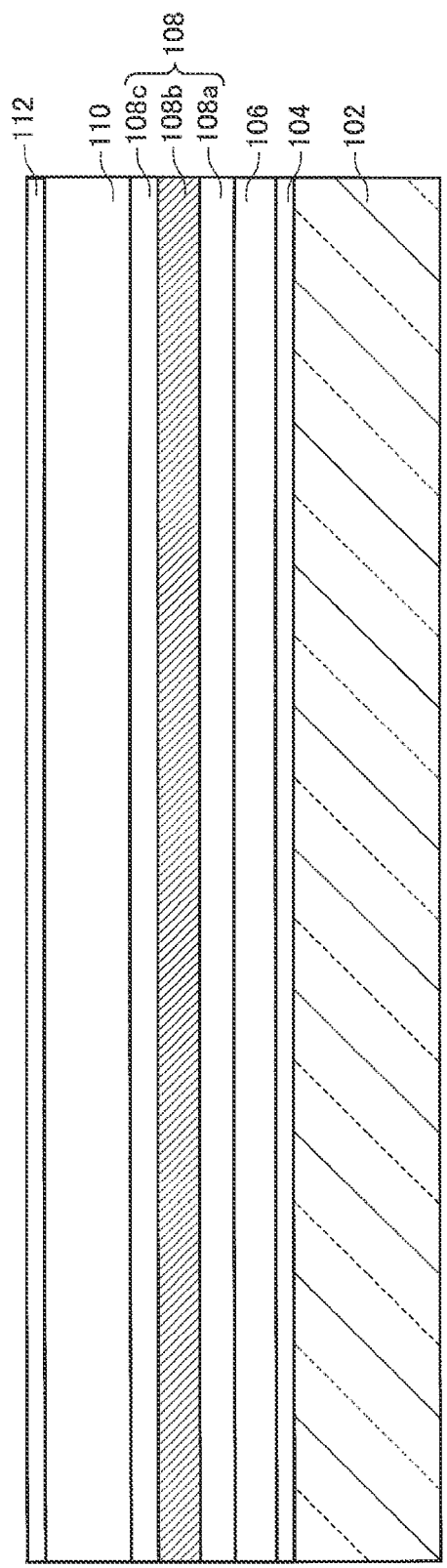
FIG. 16 is a cross-sectional view schematically illustrating manufacturing steps of the short optical pulse generator according to the second embodiment.
Figure 17:
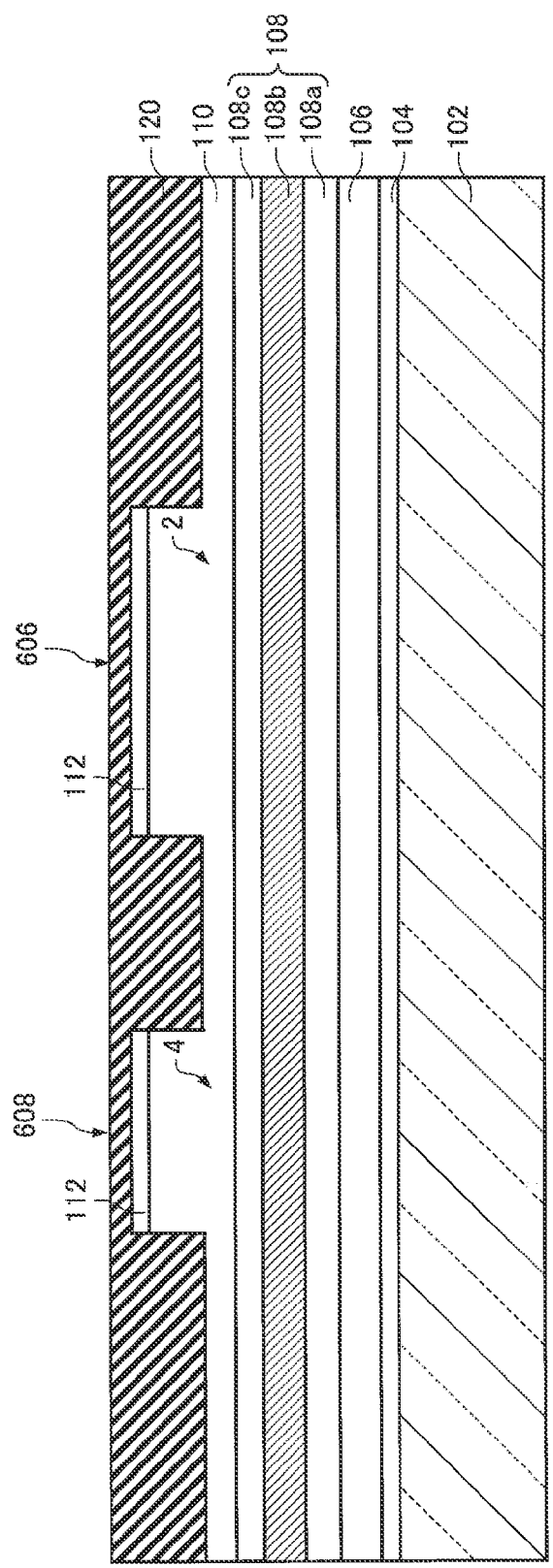
FIG. 17 is a cross-sectional view schematically illustrating manufacturing steps of the short optical pulse generator according to the second embodiment.

Next, a manufacturing method of the short optical pulse generator according to the present embodiment will be described with reference to the drawings. FIGS. 16 and 17 are cross-sectional views schematically illustrating manufacturing steps of the short optical pulse generator 600 according to the present embodiment. In addition, FIGS. 16 and 17 correspond to FIG. 15.

As shown in FIG. 16, the buffer layer 104, the first clad layer 106, the first core layer 108, the second clad layer 110, and the cap layer 112 are epitaxially grown in this order on the substrate 102. In addition, if the first core layer 108 is to be formed, a periodic structure is formed in the second guide layer 108c in the same manner as in the above-described manufacturing method of the short optical pulse generator 100.

As shown in FIG. 17, the cap layer 112 and the second clad layer 110 are etched so as to form the columnar sections 606 and 608. Next, the insulating layer 120 is formed on the lateral sides of the columnar sections 606 and 608 and on the columnar sections 606 and 608.

As shown in FIG. 14, the second electrode 132 is formed on the cap layer 112 of the upper side of the first region 102a. Next, the first electrode 130 is formed on the lower surface of the substrate 102.

Through the above-described steps, the short optical pulse generator 600 can be manufactured.

According to the manufacturing method of the short optical pulse generator 600, it is possible to obtain the short optical pulse generator 600 having a reduced size.

3. Third Embodiment

Figure 18:
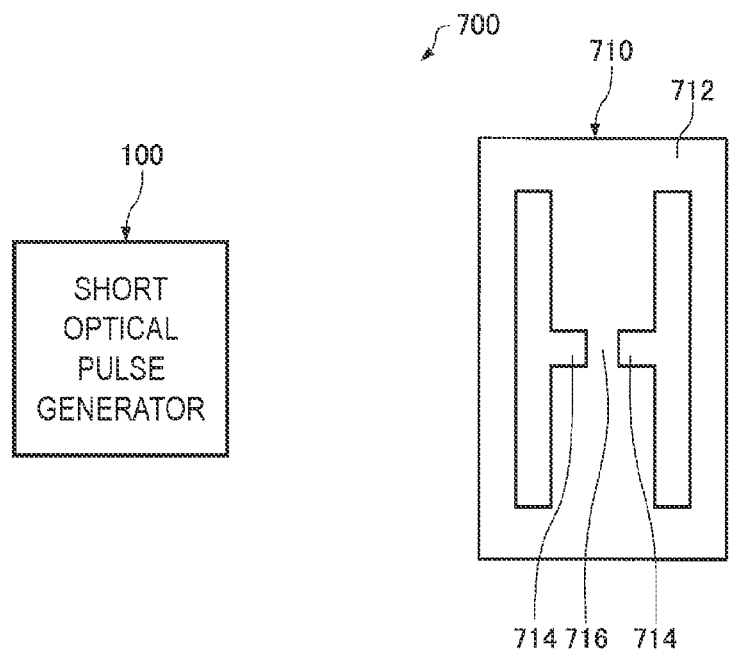
FIG. 18 is a diagram illustrating a configuration of a terahertz wave generation device according to a third embodiment.

Next, a terahertz wave generation device 700 according to a third embodiment will be described with reference to the drawings. FIG. 18 is a diagram illustrating a configuration of the terahertz wave generation device 700 according to the third embodiment.

The terahertz wave generation device 700 includes the short optical pulse generator 100 according to the embodiment of the invention and a photoconductive antenna 710 as shown in FIG. 18. Here, a description will be made of a case of using the short optical pulse generator 100 as a short optical pulse generator according to the embodiment of the invention.

The short optical pulse generator 100 generates a short optical pulse (the optical pulse P3 shown in FIG. 5) which is excitation light. A pulse width of a short optical pulse generated by the short optical pulse generator 100 is, for example, 1 fs or more and 800 fs or less.

The photoconductive antenna 710 is irradiated with the short optical pulse generated by the short optical pulse generator 100 so as to generate a terahertz wave. In addition, the terahertz wave indicates an electromagnetic wave of which a frequency is 100 GHz or more and 30 THz or less, particularly, 300 GHz or more and 3 THz or less.

The photoconductive antenna 710 is a dipole-shaped photoconductive antenna (PCA). The photoconductive antenna 710 includes a substrate 712 which is a semiconductor substrate, and a pair of electrodes 714 which are provided on the substrate 712 and are disposed opposite to each other with a gap 716. When an optical pulse is applied between the electrodes 714, the photoconductive antenna 710 generates a terahertz wave.

The substrate 712 has, for example, a semi-insulating GaAs (SI-GaAs) substrate and a low temperature growth GaAs (LT-GaAs) layer provided on the SI-GaAs substrate. A material of the electrodes 714 is, for example, Au. A distance between a pair of electrodes 714 is not particularly limited, and is appropriately set depending on conditions. A distance between a pair of electrodes 714 is, for example, 1 µm or more and 10 µm or less.

In the terahertz wave generation device 700, first, the short optical pulse generator 100 generates a short optical pulse which is emitted toward the gap 716 of the photoconductive antenna 710. The short optical pulse emitted from the short optical pulse generator 100 is applied to the gap 716 of the photoconductive antenna 710. In the photoconductive antenna 710, the gap 716 is irradiated with the short optical pulse and thus free electrons are excited. In addition, the free electrons are accelerated by applying a voltage between the electrodes 714. Thus, a terahertz wave is generated.

The terahertz wave generation device 700 includes the short optical pulse generator 100 and thus can be miniaturized.

4. Fourth Embodiment

Figure 19:
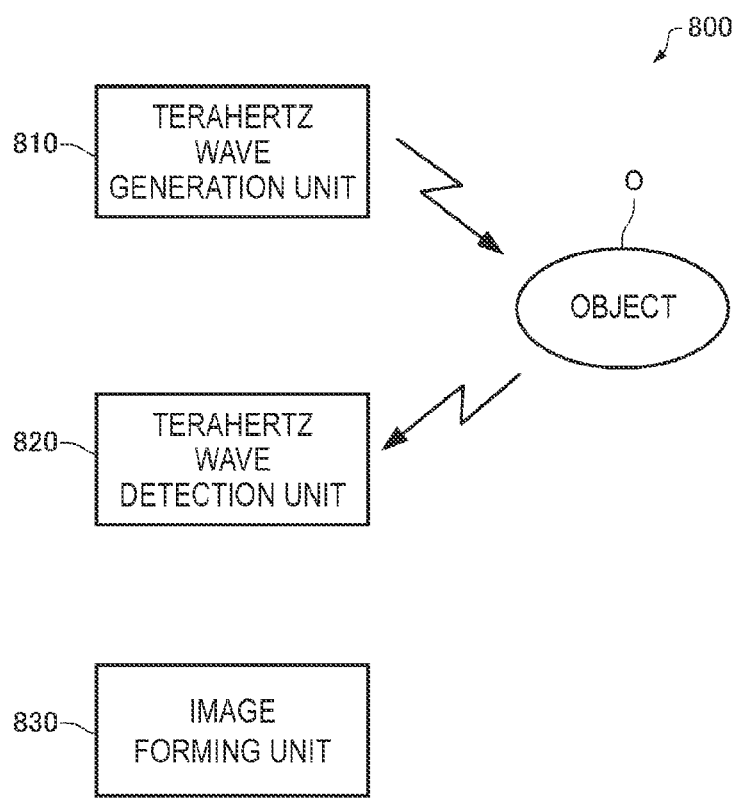
FIG. 19 is a block diagram illustrating an imaging apparatus according to a fourth embodiment.
Figure 20:
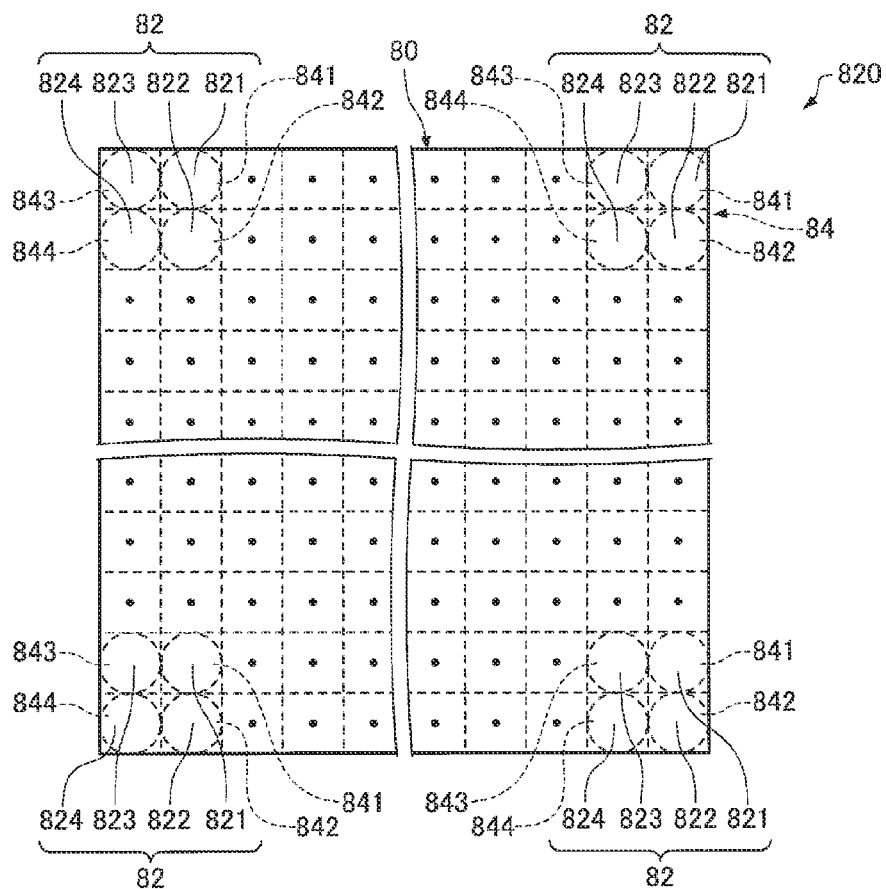
FIG. 20 is a plan view schematically illustrating a terahertz wave detection unit of the imaging apparatus according to the fourth embodiment.
Figure 21:
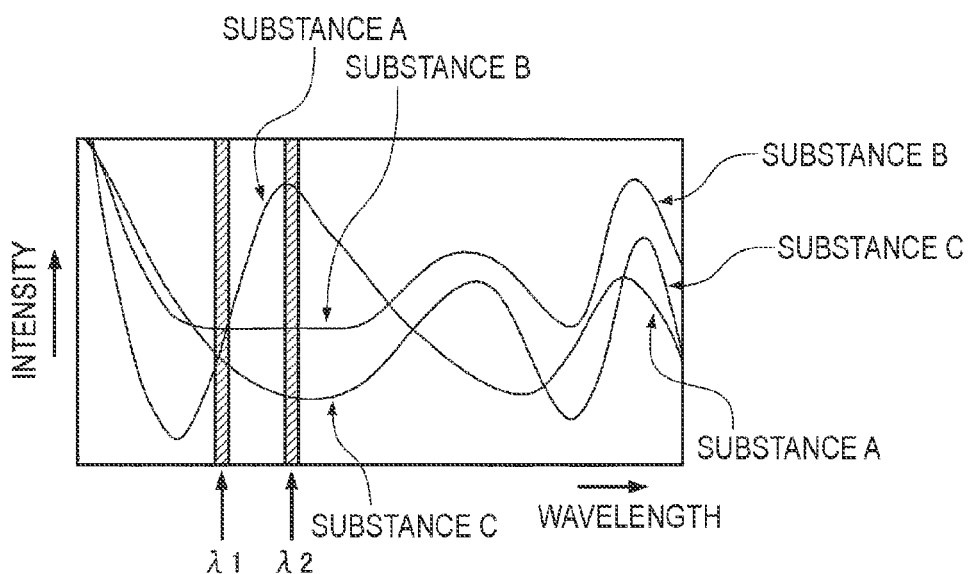
FIG. 21 is a graph illustrating spectra of an object in a terahertz band.
Figure 22:
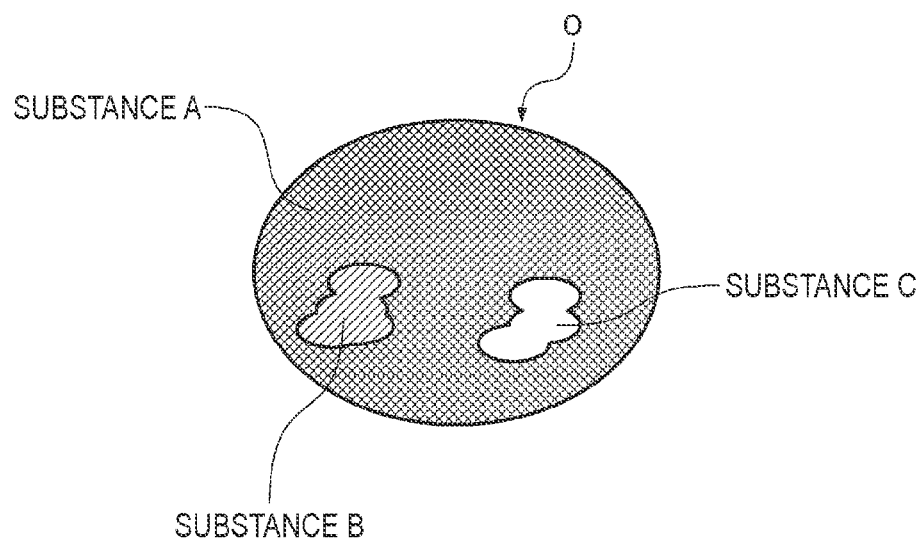
FIG. 22 is an image view illustrating a distribution of substances A, B and C of the object.

Next, an imaging apparatus 800 according to a fourth embodiment will be described with reference to the drawings. FIG. 19 is a block diagram illustrating the imaging apparatus 800 according to the fourth embodiment. FIG. 20 is a plan view schematically illustrating a terahertz wave detection unit 820 of the imaging apparatus 800. FIG. 21 is a graph illustrating spectra of an object in a terahertz band. FIG. 22 is an image view illustrating a distribution of substances A, B and C of the object.

The imaging apparatus 800 includes, as shown in FIG. 19, a terahertz wave generation unit 810 generating a terahertz wave, a terahertz wave detection unit 820 detecting a terahertz wave which is emitted from the terahertz wave generation unit 810 and is transmitted through an object O or reflected by the object O, and an image forming unit 830 generating an image of the object O, that is, image data based on a detection result from the terahertz wave detection unit 820.

As the terahertz wave generation unit 810, the terahertz wave generation device according to the embodiment of the invention may be used. Here, a description will be made of a case of using the terahertz wave generation device 700 as a terahertz wave generation device according to the embodiment of the invention.

The terahertz wave detection unit 820 uses a device including a filter 80 which passes a terahertz wave of a targeted wavelength, and a detector 84 detecting the terahertz wave of the targeted wavelength which has passed through the filter 80. In addition, the detector 84 uses a unit which converts a terahertz wave into heat so as to perform detection, that is, can convert a terahertz wave into heat and detect energy (intensity) of the terahertz wave. This detection unit may include, for example, a pyroelectric sensor, a bolometer, and the like. In addition, a configuration of the terahertz wave detection unit 820 is not limited to the above-described configuration.

In addition, the filter 80 includes a plurality of pixels (unit filter portion) 82 arranged in a two-dimensional manner. In other words, the respective pixels 82 are arranged in a matrix.

In addition, each pixel 82 has a plurality of regions which pass terahertz waves of different wavelengths, that is, a plurality of regions where wavelengths (hereinafter, referred to as "pass wavelengths") of passed terahertz waves are different. In addition, in the configuration shown in the figure, each pixel 82 has a first region 821, a second region 822, a third region 823, and a fourth region 824.

In addition, the detector 84 includes a first unit detection portion 841, a second unit detection portion 842, a third unit detection portion 843, and a fourth unit detection portion 844 which are respectively provided so as to correspond to the first region 821, the second region 822, the third region 823, and the fourth region 824 of each pixel 82 of the filter 80. The first unit detection portion 841, the second unit detection portion 842, the third unit detection portion 843, and the fourth unit detection portion 844 respectively convert terahertz waves which have passed through the first region 821, the second region 822, the third region 823, and the fourth region 824 of each pixel 82, into heat so as to perform detection. Thus, it is possible to reliably detect terahertz waves of four targeted wavelengths in each pixel 82.

Next, a usage example of the imaging apparatus 800 will be described.

First, it is assumed that an object O which is a target of spectral imaging includes three substances A, B and C. The imaging apparatus 800 performs spectral imaging on the object O. In addition, here, as an example, the terahertz wave detection unit 820 detects a terahertz wave reflected by the object O.

In addition, the first region 821 and the second region 822 are assumed to be used in each pixel 82 of the filter 80 of the terahertz wave detection unit 820. When a pass wavelength of the first region 821 is set to $\lambda 1$, a pass wavelength of the second region 822 is set to $\lambda 2$, the intensity of a component of the wavelength $\lambda 1$ of a terahertz wave reflected by the object O is set to $\alpha 1$, and the intensity of a component of the wavelength $\lambda 2$ of a terahertz wave reflected by the object O is set to $\alpha 2$, the pass wavelength $\lambda 1$ of the first region 821 and the pass wavelength $\lambda 2$ of the second region 822 are set such that a difference ($\alpha 2 - \alpha 1$) between the intensity $\alpha 2$ and the intensity $\alpha 1$ can be notably differentiated in the substance A, the substance B, and the substance C.

As shown in FIG. 21, in the substance A, the difference ($\alpha 2 - \alpha 1$) between the intensity $\alpha 2$ of the component of the wavelength $\lambda 2$ and the intensity $\alpha 1$ of the component of the wavelength $\lambda 1$ reflected by the object O is a positive value. In addition, in the substance B, the difference ($\alpha 2 - \alpha 1$) between the intensity $\alpha 2$ and the intensity $\alpha 1$ is 0. Further, in the substance C, the difference ($\alpha 2 - \alpha 1$) between the intensity $\alpha 2$ and the intensity $\alpha 1$ is a negative value.

When spectral imaging is performed on the object O by the imaging apparatus 800, first, terahertz waves are generated by the terahertz wave generation unit 810, and the object O is irradiated with the terahertz waves. In addition, the terahertz waves reflected by the object O are detected as $\alpha 1$ and $\alpha 2$ by the terahertz wave detection unit 820. This detection result is sent to the image forming unit 830. Further, application of terahertz waves to the object O and detection of terahertz waves reflected by the object O are performed on the entire object O.

The image forming unit 830 obtains the difference ($\alpha 2 - \alpha 1$) between the intensity $\alpha 2$ of the component of the wavelength $\lambda 2$ of the terahertz wave which has passed through the second region 822 of the filter 80 and the intensity $\alpha 1$ of the component of the wavelength $\lambda 1$ of the terahertz wave which has passed through the first region 821 on the basis of the detection result. In addition, in the object O, it is determined that a part for which the difference is a positive value is the substance A, a part for which the difference is 0 is the substance B, and a part for which the difference is a negative value is the substance C, so as to be specified.

In addition, the image forming unit 830 creates image data of an image showing a distribution of the substances A, B and C of the object O as shown in FIG. 22. The image data is sent to a monitor (not shown) from the image forming unit 830, and an image showing a distribution of the substances A, B and C of the object O is displayed on the monitor. In this case, for example, a region where the substance A of the object O is displayed black, a region where the substance B is displayed gray, and region where the substance C is displayed white, so as to be differentiated from each other. In this imaging apparatus 800, as described above, it is possible to realize identification of each substance constituting the object O and measurement of a distribution of each substance together.

In addition, usage of the imaging apparatus 800 is not limited to the above description, and, for example, a terahertz wave is applied to a person, the terahertz wave which has been transmitted through or reflected by the person is detected, and the detected terahertz wave is processed by the image forming unit 830, such that it is determined whether or not the person carries a gun, a knife, illegal drugs, or the like.

The imaging apparatus 800 includes the short optical pulse generator 100 and thus can be reduced in size.

5. Fifth Embodiment

Figure 23:
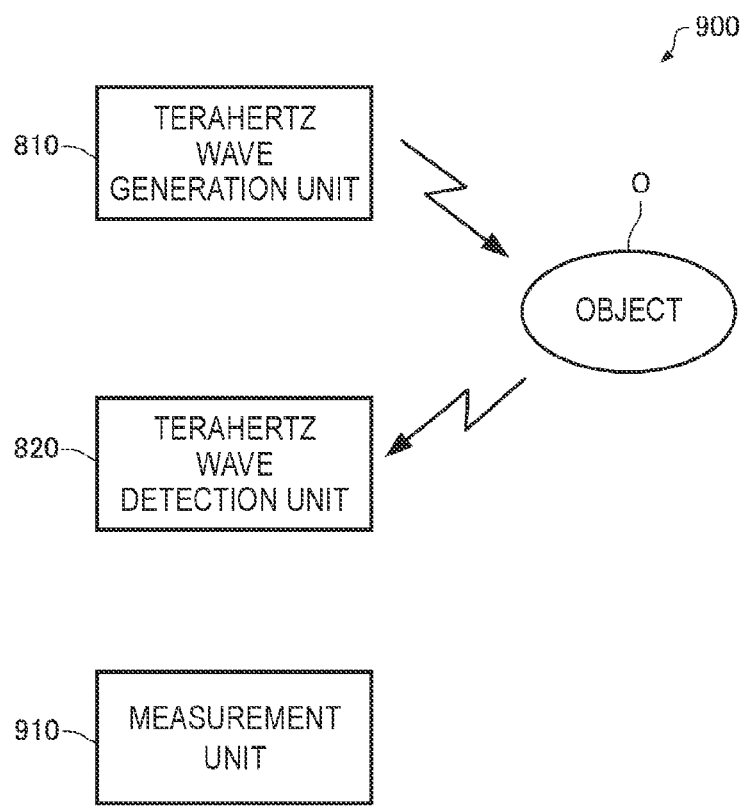
FIG. 23 is a block diagram illustrating a measurement apparatus according to a fifth embodiment.

Next, a measurement apparatus 900 according to a fifth embodiment will be described with reference to the drawings. FIG. 23 is a block diagram illustrating the measurement apparatus 900 according to the fifth embodiment. In the measurement apparatus 900 according to the present embodiment described below, a member having the same function as the constituent member of the above-described imaging apparatus 800 is given the same reference numeral, and detailed description thereof will be omitted.

The measurement apparatus 900 includes, as shown in FIG. 23, a terahertz wave generation unit 810 generating a terahertz wave, a terahertz wave detection unit 820 detecting a terahertz wave which is emitted from the terahertz wave generation unit 810 and is transmitted through an object O or a terahertz wave reflected by the object O, and a measurement unit 910 measuring the object O based on a detection result from the terahertz wave detection unit 820.

Next, a usage example of the measurement apparatus 900 will be described. When spectroscopic measurement is performed on the object O by the measurement apparatus 900, first, terahertz waves are generated by the terahertz wave generation unit 810, and the object O is irradiated with the terahertz waves. In addition, the terahertz wave detection unit 820 detects terahertz waves transmitted through the object O and terahertz waves reflected by the object O. This detection result is sent to the measurement unit 910. Further, application of terahertz waves to the object O and detection of terahertz waves transmitted through the object O or terahertz waves reflected by the object O are performed on the entire object O.

The measurement unit 910 grasps the intensity of each of terahertz waves which have respectively passed through the first region 821, the second region 822, the third region 823, and the fourth region 824 of each pixel 82 of the filter 80, from the detection result, and analyzes components of the object O and a distribution thereof.

The measurement apparatus 900 includes the short optical pulse generator 100 and thus can be miniaturized.

6. Sixth Embodiment

Figure 24:
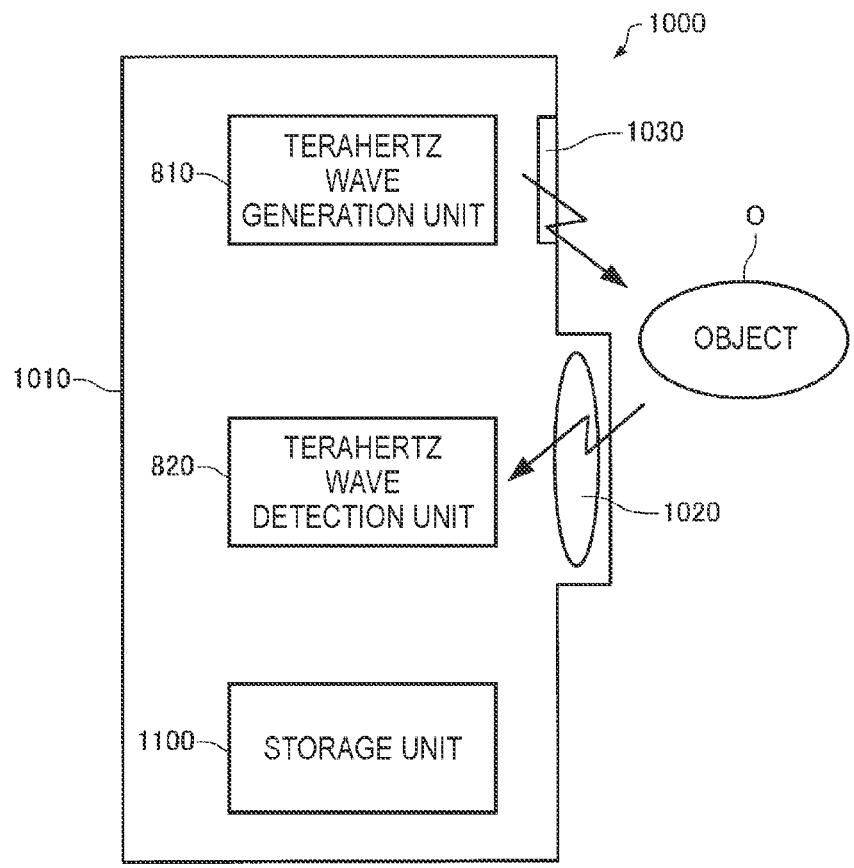
FIG. 24 is a block diagram illustrating a camera according to a sixth embodiment.
Figure 25:
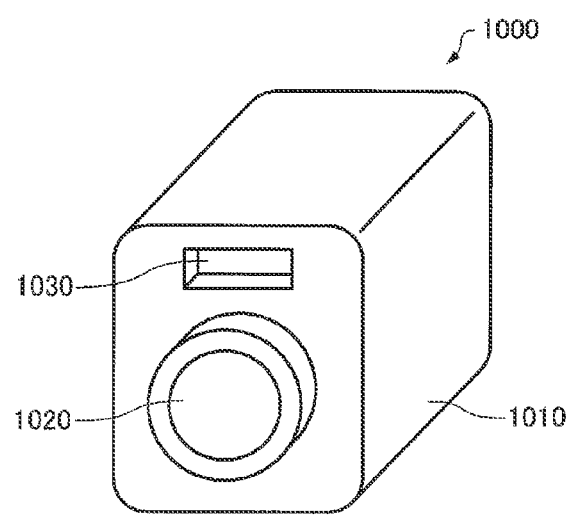
FIG. 25 is a perspective view schematically illustrating the camera according to the sixth embodiment.

Next, a camera 1000 according to a sixth embodiment will be described with reference to the drawings. FIG. 24 is a block diagram illustrating the camera 1000 according to the sixth embodiment. FIG. 25 is a perspective view schematically illustrating the camera 1000. In the camera 1000 according to the present embodiment described below, a member having the same function as the constituent member of the above-described imaging apparatus 800 is given the same reference numeral, and detailed description thereof will be omitted.

The camera 1000 includes, as shown in FIGS. 24 and 25, a terahertz wave generation unit 810 generating a terahertz wave, a terahertz wave detection unit 820 detecting a terahertz wave which is emitted from the terahertz wave generation unit 810 and is reflected by an object O or a terahertz wave transmitted through the object O, and a storage unit 1100. In addition, the respective devices 810, 820 and 1100 are accommodated in a casing 1010 of the camera 1000. Further, the camera 1000 includes a lens (optical system) 1020 which allows a terahertz wave reflected by the object O to converge (to form an image) on the terahertz wave detection unit 820, and a window portion 1030 which emits a terahertz wave generated by the terahertz wave generation unit 810 to outside of the casing 1010. The lens 1020 or the window portion 1030 is formed by a member such as silicon, quartz, or polyethylene which transmits or refracts a terahertz wave. In addition, the window portion 1030 may have a configuration in which an opening is just provided such as a slit.

Next, a usage example of the camera 1000 will be described. When the object O is imaged by the camera 1000, first, terahertz waves are generated by the terahertz wave generation unit 810, and the object O is irradiated with the terahertz waves. In addition, the lens 1020 allows terahertz waves reflected by the object O to converge (to form an image) on the terahertz wave detection unit 820 so as to perform detection. This detection result is sent to the storage unit 1100. Further, application of terahertz waves to the object O and detection of terahertz waves reflected by the object O are performed on the entire object O. In addition, the detection result may be transferred to an external apparatus such as a personal computer. The personal computer may perform various processes based on the detection result.

The above-described embodiments and modification examples are only an example, and the invention is not limited thereto. For example, the respective embodiments and modification examples may be appropriately combined.

The invention includes the substantially same configuration (for example, a configuration in which a function, a method, and a result are the same, or a configuration in which an object and an effect are the same) as the configuration described in the embodiments. In addition, the invention includes a configuration in which an unessential part of the configuration described in the embodiments is replaced. Further, the invention includes a configuration which achieves the same operation and effect or can achieve the same object as the configuration described in the embodiments. Furthermore, the invention includes a configuration in which a well-known technique is added to the configuration described in the embodiments.

What is claimed is:

1. A short optical pulse generator comprising:
an optical pulse generation portion that has a quantum well structure and generates an optical pulse;
a frequency chirp portion that has a quantum well structure and chirps a frequency of the optical pulse such that when the optical pulse propagates through the frequency chirp portion, a frequency of the optical pulse varies with time and a chirped optical pulse;
a group velocity dispersion portion that includes a plurality of optical waveguides disposed in a mode coupling distance and which causes pulse compression based on a group velocity difference of the chirped optical pulse, and
a substrate,
wherein the optical pulse generation portion, the frequency chirp portion, and the group velocity dispersion portion are all provided on the said substrate.

2. The short optical pulse generator according to claim 1, wherein the group velocity dispersion portion is made of a semiconductor material.

3. The short optical pulse generator according to claim 1, wherein a layer having a quantum well structure of the optical pulse generation portion and a layer having a quantum well structure of the frequency chirp portion are the same layer.

4. The short optical pulse generator according to claim 3, wherein a forward bias voltage is applied in the optical pulse generation portion and a reverse bias voltage is applied in the frequency chirp portion.

5. The short optical pulse generator according to claim 1, wherein a quantum well structure of the frequency chirp portion and a core layer forming at least one of the plurality of optical waveguides comprise the same layer.

6. The short optical pulse generator according to claim 1, wherein the group velocity dispersion portion includes a plurality of laminated semiconductor layers, and the plurality of optical waveguides are arranged in a laminate direction of the semiconductor layers.

7. The short optical pulse generator according to claim 1, wherein the group velocity dispersion portion includes a plurality of laminated semiconductor layers, and the plurality of optical waveguides are arranged in a direction perpendicular to a laminate direction of the semiconductor layers.

8. The short optical pulse generator according to claim 1, wherein each of the optical pulse generation portion, the frequency chirp portion, and the group velocity dispersion portion includes a plurality of semiconductor layers made of an AlGaAs based material.

9. A terahertz wave generation device comprising:
the short optical pulse generator according to claim 1; and
a photoconductive antenna that is irradiated with a short optical pulse generated by the short optical pulse generator so as to generate a terahertz wave.

10. A terahertz wave generation device comprising:
the short optical pulse generator according to claim 2; and
a photoconductive antenna that is irradiated with a short optical pulse generated by the short optical pulse generator so as to generate a terahertz wave.

11. A terahertz wave generation device comprising:
the short optical pulse generator according to claim 3; and
a photoconductive antenna that is irradiated with a short optical pulse generated by the short optical pulse generator so as to generate a terahertz wave.

12. A camera comprising:
the short optical pulse generator according to claim 1;
a photoconductive antenna that is irradiated with a short optical pulse generated by the short optical pulse generator so as to generate a terahertz wave;
a terahertz wave detection unit that detects the terahertz wave emitted from the photoconductive antenna and transmitted through an object or reflected by the object; and
a storage unit that stores a detection result from the terahertz wave detection unit.

13. A camera comprising:
the short optical pulse generator according to claim 2;
a photoconductive antenna that is irradiated with a short optical pulse generated by the short optical pulse generator so as to generate a terahertz wave;
a terahertz wave detection unit that detects the terahertz wave emitted from the photoconductive antenna and transmitted through an object or reflected by the object; and
a storage unit that stores a detection result from the terahertz wave detection unit.

14. A camera comprising:
the short optical pulse generator according to claim 3;
a photoconductive antenna that is irradiated with a short optical pulse generated by the short optical pulse generator so as to generate a terahertz wave;
a terahertz wave detection unit that detects the terahertz wave emitted from the photoconductive antenna and transmitted through an object or reflected by the object; and
a storage unit that stores a detection result from the terahertz wave detection unit.

15. An imaging apparatus comprising:
the short optical pulse generator according to claim 1;
a photoconductive antenna that is irradiated with a short optical pulse generated by the short optical pulse generator so as to generate a terahertz wave;
a terahertz wave detection unit that detects the terahertz wave emitted from the photoconductive antenna and transmitted through an object or reflected by the object; and
an image forming unit that generates an image of the object based on a detection result from the terahertz wave detection unit.

16. An imaging apparatus comprising:
the short optical pulse generator according to claim 2;
a photoconductive antenna that is irradiated with a short optical pulse generated by the short optical pulse generator so as to generate a terahertz wave;
a terahertz wave detection unit that detects the terahertz wave emitted from the photoconductive antenna and transmitted through an object or reflected by the object; and
an image forming unit that generates an image of the object based on a detection result from the terahertz wave detection unit.

17. An imaging apparatus comprising:
the short optical pulse generator according to claim 3;
a photoconductive antenna that is irradiated with a short optical pulse generated by the short optical pulse generator so as to generate a terahertz wave;
a terahertz wave detection unit that detects the terahertz wave emitted from the photoconductive antenna and transmitted through an object or reflected by the object; and
an image forming unit that generates an image of the object based on a detection result from the terahertz wave detection unit.

18. A measurement apparatus comprising:
the short optical pulse generator according to claim 1;
a photoconductive antenna that is irradiated with a short optical pulse generated by the short optical pulse generator so as to generate a terahertz wave;
a terahertz wave detection unit that detects the terahertz wave emitted from the photoconductive antenna and transmitted through an object or reflected by the object; and
a measurement unit that measures the object based on a detection result from the terahertz wave detection unit.

19. A measurement apparatus comprising:
the short optical pulse generator according to claim 2;
a photoconductive antenna that is irradiated with a short optical pulse generated by the short optical pulse generator so as to generate a terahertz wave;
a terahertz wave detection unit that detects the terahertz wave emitted from the photoconductive antenna and transmitted through an object or reflected by the object; and
a measurement unit that measures the object based on a detection result from the terahertz wave detection unit.

20. A measurement apparatus comprising:
the short optical pulse generator according to claim 3;
a photoconductive antenna that is irradiated with a short optical pulse generated by the short optical pulse generator so as to generate a terahertz wave;
a terahertz wave detection unit that detects the terahertz wave emitted from the photoconductive antenna and transmitted through an object or reflected by the object; and
a measurement unit that measures the object based on a detection result from the terahertz wave detection unit.

* * * * *